(12) United States Patent
Little et al.

(10) Patent No.: US 7,901,677 B1
(45) Date of Patent: Mar. 8, 2011

(54) USE OF AN ANTIBODY AGAINST THE LAMININ RECEPTOR OR LAMININ RECEPTOR PRECURSOR FOR THE TREATMENT OR DIAGNOSIS OF SEVERAL CANCER TYPES

(75) Inventors: Melvyn Little, Neckargemünd (DE); Stefan Knackmuss, Plankstadt (DE); Uwe Reusch, Maikammer (DE); Sergey Kipriyanov, Quedlinburg (DE); Fabrice Le Gall, Edingen-Neckarhausen (DE); Vera Mick, Schifferstadt (DE); Karin Hoffmann, Schwetzingen (DE); Peter Röttgen, Ladenburg (DE)

(73) Assignee: Affimed Therapeutics AG, Heidelberg (DE)

( * ) Notice: Subject to any disclaimer, the term of this patent is extended or adjusted under 35 U.S.C. 154(b) by 43 days.

(21) Appl. No.: 11/910,478

(22) PCT Filed: Apr. 5, 2006

(86) PCT No.: PCT/EP2006/003104
§ 371 (c)(1),
(2), (4) Date: Nov. 29, 2007

(87) PCT Pub. No.: WO2006/105954
PCT Pub. Date: Oct. 12, 2006

(30) Foreign Application Priority Data

Apr. 5, 2005 (EP) ..................................... 05007380

(51) Int. Cl.
*A61K 39/395* (2006.01)
*A61K 35/12* (2006.01)

(52) U.S. Cl. ................ 424/130.1; 424/141.1; 424/143.1; 424/277.1

(58) Field of Classification Search .......................... None
See application file for complete search history.

(56) References Cited

U.S. PATENT DOCUMENTS

| | | | | |
|---|---|---|---|---|
| 5,637,481 | A * | 6/1997 | Ledbetter et al. | 435/69.6 |
| 2003/0091569 | A1 * | 5/2003 | Gerritsen et al. | 424/146.1 |
| 2004/0180002 | A1 * | 9/2004 | Young et al. | 424/1.49 |
| 2005/0244899 | A1 * | 11/2005 | Young et al. | 435/7.2 |

FOREIGN PATENT DOCUMENTS

WO WO 2005/035580 A 4/2005

OTHER PUBLICATIONS

Belkin et al, Microscropy research and technique, 51: 280-302, 2000.*
Mesh word search result for Laminin receptor (2009).*
Paul, Fundamental Immunology, 3rd Edition, 1993, pp. 292-295.*
Rudikoff et al., Proc. Natl. Acad. Sci. USA 1982 vol. 79: p. 1979.*
Casset et al, BBRC 307, 198-205 2003.*
Pascalis et al, (The Journal of Immunology vol. 169, 3076-3084, 2002.*
Kipriyanov et al , JMB, 293: 41-56, 1999.*
Rudikoff et al , Proc Natl Acad Sci USA, 79: 1979, 1982.*
International Search Report: PCT/EP2006/003104 mailed Jan. 18, 2007.
Narumi Koh et al.: "Inhibition of Experimental Metastasis of Human Fibrosarcoma Cells by Anti-Recombinant 37-kDa Laminin Binding Protein Antibody", Japanese Journal of Cancer Research, vol. 90, No. 4, Apr. 1999, pp. 425-431.
Xie M et al,: "Expression and Function of Laminin Receptor in Laryngeal Squamous Cell Carcinoma", Zhonghua Zhongliu Zazhi—Chinese Journal of Oncology, Zhonghua Yixuehui, Beijing, CN, vol. 26, No. 9, Sep. 23, 2004, pp. 539-542. With English abstract.
Zhonghua Bing Li Xue Za Zhi, Chinese Journal of Pathology, Aug. 1993, vol. 22. No. 4, Aug. 1993, pp. 207-210. With English abstract.
Isemura Mamoru et al.; "Immunohistochemical Detection of the Laminin Receptor Polypeptide, a Putative Precursor of 67 kDa-Laminin Receptor, In Human Lung Cancer", International Journal of Oncology, vol. 7, No. 1, 1995, pp. 123-126.
Nihon Ky Bu Shikkan Gakkai Zasshi, Dec. 1992, vol. 30 Suppl, Dec. 1992, pp. 92-97.
Viacava P. at al.: "The Spectrum of 67-kD Laminin Receptor Expression in Breast Carcinoma Progression", Journal of Pathology, Chichester, Sussex, GB, vol. 182, No. 1, May 1997, pp. 36-44.
Martignone S et al.; "Characterization of Two Monoclonal Antibodies Directed against the 67 kDa High Affinity Laminin Receptor and Application for the Study of Breast Carcinoma Progression", Clinical and Experimental Metastasis, vol. 10, No. 6, 1992, pp. 379-386.
Liotta L A et al,: "Monoclonal Antibodies to the Human Laminin Receptor Recognize Structurally Distinct Sites", Experimental Cell Research, vol. 156, No. 1, 1985, pp. 117-126.
Chantal Zuber, et al.: "Invasion of Tumorigenic HT1080 Cells Is Impeded by Blocking or Downregulating the 37-kDa/67-kDa Laminin Receptor", J. Mol, Biol. (2008) 378, pp. 530-539.

\* cited by examiner

*Primary Examiner* — Misook Yu
*Assistant Examiner* — Lei Yao
(74) *Attorney, Agent, or Firm* — Howrey LLP; Viola T. Kung

(57) ABSTRACT

Described is the use of a recombinant antibody comprising a binding site specific for an epitope of the laminin receptor or laminin receptor precursor for the treatment or diagnosis of various cancers, particularly B-CLL. Preferably, this antibody additionally comprises a binding site for at least one particular cell surface antigen.

13 Claims, 16 Drawing Sheets

Figure 6a:

scFv N3

$V_H$

EVQLVESGGGVVQPGRSLRLSCAASGFTFSSYGMHWVRQAPGKGLEWVAVIWYDGSNKYYADSVKGRFTISRDNSKNTLYLQMNSLRAEDT
                              |—CDR1—|                |————————CDR2————————|

AVYYCATIPRSSFYYGMDVWQGTTVTVSSGSASAPTL    (SEQ ID NO:4)
    |———CDR3———|

$V_L$

QPVLTQPPSASGTPGQRVTISCSGSRSNIGSNTVNWYQQLPGTAPKLLIYGNNQRPSGVPERFSGKSGTSASLAISGLQSEDEADYYCAA
                       |——CDR1——|                  |—CDR2—|

WDDSLTGVLFGGGTKLTVLGQPKAAPSVTLFPPS    (SEQ ID NO:5)
|——CDR3——|

Figure 6b scFv S18

$V_H$

QVQLQESGGGLVQPGGSLRLSCAASGFMFSRYAMSWVRQAPGKGPEWVSGISGSGGSTYYADSVKGRFTVSRDNSKNTLYLQMNSLRAEDT

AVYYCARHPGFWHFDYWGQGTLVTVSSGSASAP (SEQ ID NO: 6)

$V_L$

SELTQDPAVSVALGQTVRITCQGDSLRNFYASWYQQKPGQAPTLVIYGLSKRPSGIPDRFSASSSGNTASLTITGAQAEDEADYYCNSRDR

SGNHVNVLFGGGTKLTVLRQPKAAPSVTLFPPSS (SEQ ID NO: 7)

Figure 7

```
              Frame 3      CDR3      Frame 4
S18           DEADYYCNSR R  GNHVNVLFGGG   (SEQ ID NO:118)
5-4-19        DEADYYCNSRAD--  VLFGGG      (SEQ ID NO:119)
5-4-1         DEADYYCNSR  --  VLFGGG      (SEQ ID NO:120)
5-4-31 (6x)   DEADYYCSSR  --TKQVLFGGG     (SEQ ID NO:121)
5-4-16        DEADYYCNSRENN--RYSVLFGGG    (SEQ ID NO:122)
5-4-10        DEADYYCNSRTDD---PPKVLFGGG   (SEQ ID NO:123)
5-4-25        DEADYYCNSRN T--K SVLFGGG    (SEQ ID NO:124)
5-3-43        DEADYYCNSRRTH--PKMVLFGGG    (SEQ ID NO:125)
```

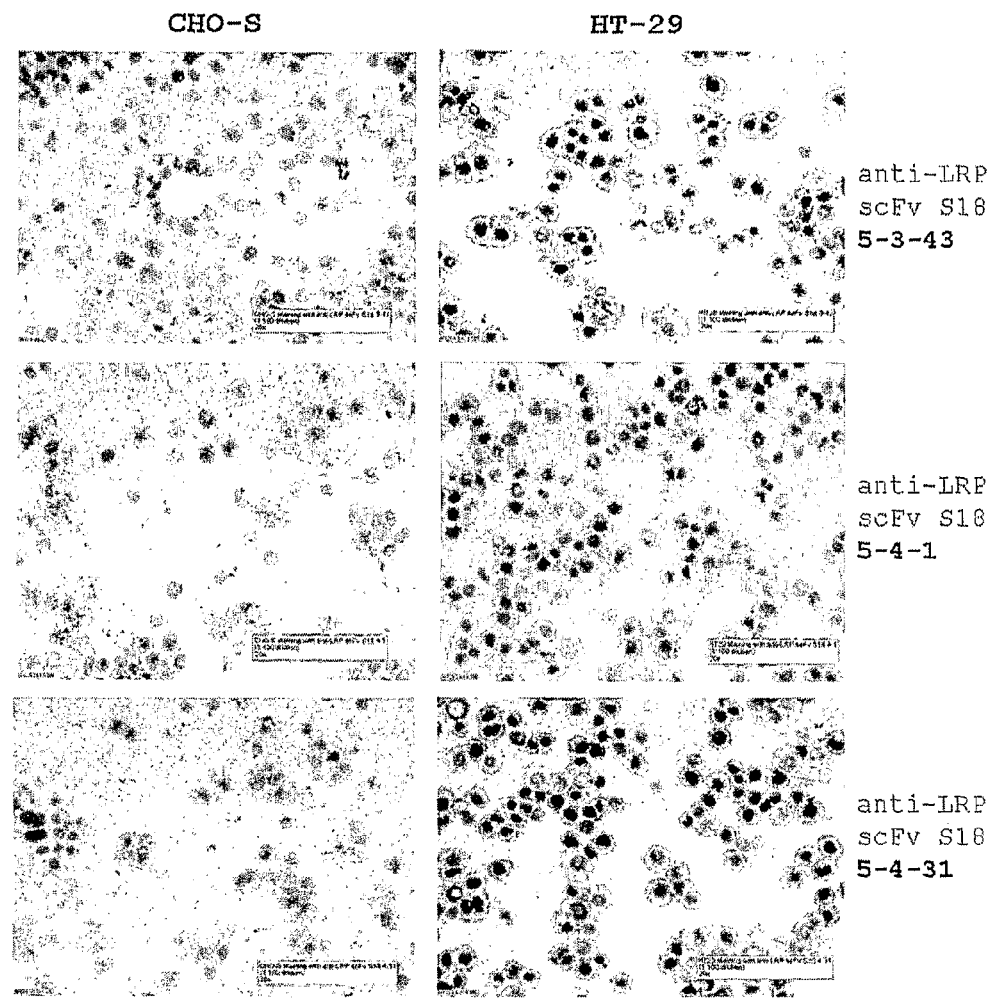
Fig. 11 (Continuation)

| | $K_D$ | Goodness of fit ($R^2$) |
|---|---|---|
| S18 parental | 5.2 nM | 0.9956 |
| 5-3-43 | 0.8 nM | 0.9962 |
| 5-4-1 | 0.6 nM | 0.9932 |
| 5-4-31 | 1.2 nM | 0.9423 |

A

B

SEQUENCE LISTING

```
<160> NUMBER OF SEQ ID NOS: 125

<210> SEQ ID NO 1
<211> LENGTH: 6
<212> TYPE: PRT
<213> ORGANISM: artificial sequence
<220> FEATURE:
<223> OTHER INFORMATION: Peptide G
```

-continued

<400> SEQUENCE: 1

Leu Met Trp Trp Met Leu
1               5

<210> SEQ ID NO 2
<211> LENGTH: 5
<212> TYPE: PRT
<213> ORGANISM: artificial sequence
<220> FEATURE:
<223> OTHER INFORMATION: LR-binding peptide

<400> SEQUENCE: 2

Tyr Ile Gly Ser Arg
1               5

<210> SEQ ID NO 3
<211> LENGTH: 17
<212> TYPE: DNA
<213> ORGANISM: artificial sequence
<220> FEATURE:
<223> OTHER INFORMATION: Synthetic sequence
<220> FEATURE:
<221> NAME/KEY: variation
<222> LOCATION: (14)..(14)
<223> OTHER INFORMATION: S = G or C

<400> SEQUENCE: 3
tgtgcgarat tgastac                                                    17

<210> SEQ ID NO 4
<211> LENGTH: 128
<212> TYPE: PRT
<213> ORGANISM: artificial sequence
<220> FEATURE:
<223> OTHER INFORMATION: scFv N3

<400> SEQUENCE: 4

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Ile Pro Arg Ser Ser Phe Tyr Tyr Gly Met Asp Val Trp Gln
            100                 105                 110

Gly Thr Thr Val Thr Val Ser Ser Gly Ser Ala Ser Ala Pro Thr Leu
        115                 120                 125

<210> SEQ ID NO 5
<211> LENGTH: 125
<212> TYPE: PRT
<213> ORGANISM: artificial sequence
<220> FEATURE:
<223> OTHER INFORMATION: scFv N3 VL

<400> SEQUENCE: 5

Gln Pro Val Leu Thr Gln Pro Pro Ser Ala Ser Gly Thr Pro Gly Gln

```
                1               5                  10                 15
Arg Val Thr Ile Ser Cys Ser Gly Ser Arg Ser Asn Ile Gly Ser Asn
                20                 25                 30

Thr Val Asn Trp Tyr Gln Gln Leu Pro Gly Thr Ala Pro Lys Leu Leu
                35                 40                 45

Ile Tyr Gly Asn Asn Gln Arg Pro Ser Gly Val Pro Glu Arg Phe Ser
                50                 55                 60

Gly Ser Lys Ser Gly Thr Ser Ala Ser Leu Ala Ile Ser Gly Leu Gln
65                                 70                 75                 80

Ser Glu Asp Glu Ala Asp Tyr Tyr Cys Ala Ala Trp Asp Asp Ser Leu
                85                 90                 95

Thr Gly Val Leu Phe Gly Gly Gly Thr Lys Leu Thr Val Leu Gly Gln
                100                105                110

Pro Lys Ala Ala Pro Ser Val Thr Leu Phe Pro Pro Ser
                115                120                125

<210> SEQ ID NO 6
<211> LENGTH: 124
<212> TYPE: PRT
<213> ORGANISM: artificial sequence
<220> FEATURE:
<223> OTHER INFORMATION: scFv S18

<400> SEQUENCE: 6

Gln Val Gln Leu Gln Glu Ser Gly Gly Gly Leu Val Gln Pro Gly Gly
1               5                  10                 15

Ser Leu Arg Leu Ser Cys Ala Ala Ser Gly Phe Met Phe Ser Arg Tyr
                20                 25                 30

Ala Met Ser Trp Val Arg Gln Ala Pro Gly Lys Gly Pro Glu Trp Val
                35                 40                 45

Ser Gly Ile Ser Gly Ser Gly Gly Ser Thr Tyr Tyr Ala Asp Ser Val
                50                 55                 60

Lys Gly Arg Phe Thr Val Ser Arg Asp Asn Ser Lys Asn Thr Leu Tyr
65                                 70                 75                 80

Leu Gln Met Asn Ser Leu Arg Ala Glu Asp Thr Ala Val Tyr Tyr Cys
                85                 90                 95

Ala Arg His Pro Gly Phe Trp His Phe Asp Tyr Trp Gly Tyr Gly Thr
                100                105                110

Leu Val Thr Val Ser Ser Gly Ser Ala Ser Ala Pro
                115                120

<210> SEQ ID NO 7
<211> LENGTH: 125
<212> TYPE: PRT
<213> ORGANISM: artificial sequence
<220> FEATURE:
<223> OTHER INFORMATION: scFv S18 VL

<400> SEQUENCE: 7

Ser Glu Leu Thr Gln Asp Pro Ala Val Ser Val Ala Leu Gly Gln Thr
1               5                  10                 15

Val Arg Ile Thr Cys Gln Gly Asp Ser Leu Arg Asn Phe Tyr Ala Ser
                20                 25                 30

Trp Tyr Gln Gln Lys Pro Gly Gln Ala Pro Thr Leu Val Ile Tyr Gly
                35                 40                 45

Leu Ser Lys Arg Pro Ser Gly Ile Pro Asp Arg Phe Ser Ala Ser Ser
                50                 55                 60

Ser Gly Asn Thr Ala Ser Leu Thr Ile Thr Gly Ala Gln Ala Glu Asp
```

```
                65                  70                  75                  80
Glu Ala Asp Tyr Tyr Cys Asn Ser Arg Asp Arg Ser Gly Asn His Val
                    85                  90                  95
Asn Val Leu Phe Gly Gly Gly Thr Lys Leu Thr Val Leu Arg Gln Pro
                    100                 105                 110
Lys Ala Ala Pro Ser Val Thr Leu Phe Pro Pro Ser Ser
                    115                 120                 125

<210> SEQ ID NO 8
<211> LENGTH: 21
<212> TYPE: DNA
<213> ORGANISM: artificial sequence
<220> FEATURE:
<223> OTHER INFORMATION: Primer VH-1a

<400> SEQUENCE: 8
caggtgcagc tggtgcagtc t                                              21

<210> SEQ ID NO 9
<211> LENGTH: 21
<212> TYPE: DNA
<213> ORGANISM: artificial sequence
<220> FEATURE:
<223> OTHER INFORMATION: Primer VH-1b

<400> SEQUENCE: 9
caggtccagc ttgtgcagtc t                                              21

<210> SEQ ID NO 10
<211> LENGTH: 21
<212> TYPE: DNA
<213> ORGANISM: artificial sequence
<220> FEATURE:
<223> OTHER INFORMATION: Primer VH-1c

<400> SEQUENCE: 10
caggtccagc tggtacagtc t                                              21

<210> SEQ ID NO 11
<211> LENGTH: 21
<212> TYPE: DNA
<213> ORGANISM: artificial sequence
<220> FEATURE:
<223> OTHER INFORMATION: Primer VH-1d

<400> SEQUENCE: 11
gaggtccagc tggtacagtc t                                              21

<210> SEQ ID NO 12
<211> LENGTH: 21
<212> TYPE: DNA
<213> ORGANISM: artificial sequence
<220> FEATURE:
<223> OTHER INFORMATION: Primer VH-1e

<400> SEQUENCE: 12
cagatgcagc tggtacagtc t                                              21

<210> SEQ ID NO 13
<211> LENGTH: 21
<212> TYPE: DNA
<213> ORGANISM: artificial sequence
<220> FEATURE:
<223> OTHER INFORMATION: Primer VH-2a

<400> SEQUENCE: 13
```

```
cagatcacct tgaaggagtc t                                              21

<210> SEQ ID NO 14
<211> LENGTH: 21
<212> TYPE: DNA
<213> ORGANISM: artificial sequence
<220> FEATURE:
<223> OTHER INFORMATION: Primer VH-2b

<400> SEQUENCE: 14
caggtcacct tgaaggagtc t                                              21

<210> SEQ ID NO 15
<211> LENGTH: 21
<212> TYPE: DNA
<213> ORGANISM: artificial sequence
<220> FEATURE:
<223> OTHER INFORMATION: Primer VH-3

<400> SEQUENCE: 15
gaagtgcagc tggtggagtc t                                              21

<210> SEQ ID NO 16
<211> LENGTH: 21
<212> TYPE: DNA
<213> ORGANISM: artificial sequence
<220> FEATURE:
<223> OTHER INFORMATION: Primer VH-3b

<400> SEQUENCE: 16
caggtgcagc tggtggagtc t                                              21

<210> SEQ ID NO 17
<211> LENGTH: 21
<212> TYPE: DNA
<213> ORGANISM: artificial sequence
<220> FEATURE:
<223> OTHER INFORMATION: Primer VH-3c

<400> SEQUENCE: 17
gaggtgcagc tgttggagtc t                                              21

<210> SEQ ID NO 18
<211> LENGTH: 21
<212> TYPE: DNA
<213> ORGANISM: artificial sequence
<220> FEATURE:
<223> OTHER INFORMATION: Primer VH-4a

<400> SEQUENCE: 18
caggtgcagc tgcaggagtc g                                              21

<210> SEQ ID NO 19
<211> LENGTH: 21
<212> TYPE: DNA
<213> ORGANISM: artificial sequence
<220> FEATURE:
<223> OTHER INFORMATION: Primer VH-4b

<400> SEQUENCE: 19
cagctgcagc tgcaggagtc g                                              21

<210> SEQ ID NO 20
<211> LENGTH: 21
<212> TYPE: DNA
<213> ORGANISM: artificial sequence
```

```
<220> FEATURE:
<223> OTHER INFORMATION: Primer VH-4c

<400> SEQUENCE: 20
caggtgcagc tacagcagtg g                                              21

<210> SEQ ID NO 21
<211> LENGTH: 21
<212> TYPE: DNA
<213> ORGANISM: artificial sequence
<220> FEATURE:
<223> OTHER INFORMATION: Primer VH-5

<400> SEQUENCE: 21
gaagtgcagc tggtgcagtc t                                              21

<210> SEQ ID NO 22
<211> LENGTH: 21
<212> TYPE: DNA
<213> ORGANISM: artificial sequence
<220> FEATURE:
<223> OTHER INFORMATION: Primer VH-6

<400> SEQUENCE: 22
caggtacagc tgcagcagtc a                                              21

<210> SEQ ID NO 23
<211> LENGTH: 21
<212> TYPE: DNA
<213> ORGANISM: artificial sequence
<220> FEATURE:
<223> OTHER INFORMATION: Primer VH-7

<400> SEQUENCE: 23
caggtgcagc tggtgcaatc t                                              21

<210> SEQ ID NO 24
<211> LENGTH: 21
<212> TYPE: DNA
<213> ORGANISM: artificial sequence
<220> FEATURE:
<223> OTHER INFORMATION: Primer IgM

<400> SEQUENCE: 24
aagggttggg gcggatgcac t                                              21

<210> SEQ ID NO 25
<211> LENGTH: 21
<212> TYPE: DNA
<213> ORGANISM: artificial sequence
<220> FEATURE:
<223> OTHER INFORMATION: Primer Vlambda-1a

<400> SEQUENCE: 25
cagtctgtgc tgacgcagcc a                                              21

<210> SEQ ID NO 26
<211> LENGTH: 21
<212> TYPE: DNA
<213> ORGANISM: artificial sequence
<220> FEATURE:
<223> OTHER INFORMATION: Primer Vlambda-1b

<400> SEQUENCE: 26
cagtctgtgc tgacgcagcc g                                              21
```

```
<210> SEQ ID NO 27
<211> LENGTH: 21
<212> TYPE: DNA
<213> ORGANISM: artificial sequence
<220> FEATURE:
<223> OTHER INFORMATION: Primer Vlamda-2

<400> SEQUENCE: 27
cagtctgccc tgactcagcc t                                              21

<210> SEQ ID NO 28
<211> LENGTH: 21
<212> TYPE: DNA
<213> ORGANISM: artificial sequence
<220> FEATURE:
<223> OTHER INFORMATION: Primer Vlambda-3a

<400> SEQUENCE: 28
tcctatgagc tgacacagcc a                                              21

<210> SEQ ID NO 29
<211> LENGTH: 21
<212> TYPE: DNA
<213> ORGANISM: artificial sequence
<220> FEATURE:
<223> OTHER INFORMATION: Primer Vlambda-3b

<400> SEQUENCE: 29
tcctctgagc tgacacagga c                                              21

<210> SEQ ID NO 30
<211> LENGTH: 21
<212> TYPE: DNA
<213> ORGANISM: artificial sequence
<220> FEATURE:
<223> OTHER INFORMATION: Primer Vlambda-3c

<400> SEQUENCE: 30
tcctatgtgc tgacacagcc a                                              21

<210> SEQ ID NO 31
<211> LENGTH: 21
<212> TYPE: DNA
<213> ORGANISM: artificial sequence
<220> FEATURE:
<223> OTHER INFORMATION: Primer Vlambda-3d

<400> SEQUENCE: 31
tcctatgagc tgacacagct a                                              21

<210> SEQ ID NO 32
<211> LENGTH: 21
<212> TYPE: DNA
<213> ORGANISM: artificial sequence
<220> FEATURE:
<223> OTHER INFORMATION: Primer Vlambda-3e

<400> SEQUENCE: 32
tcctatgagc tgatgcagcc a                                              21

<210> SEQ ID NO 33
<211> LENGTH: 21
<212> TYPE: DNA
<213> ORGANISM: artificial sequence
<220> FEATURE:
<223> OTHER INFORMATION: Primer Vlambda-4a

<400> SEQUENCE: 33
```

```
ctgcctgtgc tgactcagcc c                                              21

<210> SEQ ID NO 34
<211> LENGTH: 21
<212> TYPE: DNA
<213> ORGANISM: artificial sequence
<220> FEATURE:
<223> OTHER INFORMATION: Primer Vlambda-4b

<400> SEQUENCE: 34
cagcctgtgc tgactcaatc a                                              21

<210> SEQ ID NO 35
<211> LENGTH: 21
<212> TYPE: DNA
<213> ORGANISM: artificial sequence
<220> FEATURE:
<223> OTHER INFORMATION: Primer Vlambda-4c

<400> SEQUENCE: 35
cagcttgtgc tgactcaatc g                                              21

<210> SEQ ID NO 36
<211> LENGTH: 21
<212> TYPE: DNA
<213> ORGANISM: artificial sequence
<220> FEATURE:
<223> OTHER INFORMATION: Primer Vlambda-4a

<400> SEQUENCE: 36
cagcctgtgc tgactcagcc a                                              21

<210> SEQ ID NO 37
<211> LENGTH: 21
<212> TYPE: DNA
<213> ORGANISM: artificial sequence
<220> FEATURE:
<223> OTHER INFORMATION: Primer Vlambda-5b

<400> SEQUENCE: 37
caggctgtgc tgactcagcc g                                              21

<210> SEQ ID NO 38
<211> LENGTH: 21
<212> TYPE: DNA
<213> ORGANISM: artificial sequence
<220> FEATURE:
<223> OTHER INFORMATION: Primer Vlambda-6

<400> SEQUENCE: 38
aattttatgc tgactcagcc c                                              21

<210> SEQ ID NO 39
<211> LENGTH: 21
<212> TYPE: DNA
<213> ORGANISM: artificial sequence
<220> FEATURE:
<223> OTHER INFORMATION: Primer Vlambda-7a

<400> SEQUENCE: 39
cagactgtgg tgactcagga g                                              21

<210> SEQ ID NO 40
<211> LENGTH: 21
<212> TYPE: DNA
<213> ORGANISM: artificial sequence
```

```
<220> FEATURE:
<223> OTHER INFORMATION: Primer Vlambda-7b

<400> SEQUENCE: 40
caggctgtgg tgactcagga g                                         21

<210> SEQ ID NO 41
<211> LENGTH: 21
<212> TYPE: DNA
<213> ORGANISM: artificial sequence
<220> FEATURE:
<223> OTHER INFORMATION: Primer Vlambda-8

<400> SEQUENCE: 41
cagactgtgg tgacccagga g                                         21

<210> SEQ ID NO 42
<211> LENGTH: 21
<212> TYPE: DNA
<213> ORGANISM: artificial sequence
<220> FEATURE:
<223> OTHER INFORMATION: Primer Vlambda-9

<400> SEQUENCE: 42
cagcctgtgc tgactcagcc a                                         21

<210> SEQ ID NO 43
<211> LENGTH: 21
<212> TYPE: DNA
<213> ORGANISM: artificial sequence
<220> FEATURE:
<223> OTHER INFORMATION: Primer Vlambda-10

<400> SEQUENCE: 43
caggcagggc tgactcagcc a                                         21

<210> SEQ ID NO 44
<211> LENGTH: 21
<212> TYPE: DNA
<213> ORGANISM: artificial sequence
<220> FEATURE:
<223> OTHER INFORMATION: Primer C-lambda

<400> SEQUENCE: 44
ggacggcggg aacagagtga c                                         21

<210> SEQ ID NO 45
<211> LENGTH: 21
<212> TYPE: DNA
<213> ORGANISM: artificial sequence
<220> FEATURE:
<223> OTHER INFORMATION: Primer Vkappa-1a

<400> SEQUENCE: 45
gacatccaga tgacccagtc t                                         21

<210> SEQ ID NO 46
<211> LENGTH: 21
<212> TYPE: DNA
<213> ORGANISM: artificial sequence
<220> FEATURE:
<223> OTHER INFORMATION: Primer Vkappa-1b

<400> SEQUENCE: 46
aacatccaga tgacccagtc t                                         21
```

```
<210> SEQ ID NO 47
<211> LENGTH: 21
<212> TYPE: DNA
<213> ORGANISM: artificial sequence
<220> FEATURE:
<223> OTHER INFORMATION: Primer Vkappa-1c

<400> SEQUENCE: 47
gccatccagt tgacccagtc t                                              21

<210> SEQ ID NO 48
<211> LENGTH: 21
<212> TYPE: DNA
<213> ORGANISM: artificial sequence
<220> FEATURE:
<223> OTHER INFORMATION: Primer Vkappa-1d

<400> SEQUENCE: 48
gacatccagt tgacccagtc t                                              21

<210> SEQ ID NO 49
<211> LENGTH: 21
<212> TYPE: DNA
<213> ORGANISM: artificial sequence
<220> FEATURE:
<223> OTHER INFORMATION: Primer Vkappa-1e

<400> SEQUENCE: 49
gccatccgga tgacccagtc t                                              21

<210> SEQ ID NO 50
<211> LENGTH: 21
<212> TYPE: DNA
<213> ORGANISM: artificial sequence
<220> FEATURE:
<223> OTHER INFORMATION: Primer Vkappa-1f

<400> SEQUENCE: 50
gtcatctgga tgacccagtc t                                              21

<210> SEQ ID NO 51
<211> LENGTH: 21
<212> TYPE: DNA
<213> ORGANISM: artificial sequence
<220> FEATURE:
<223> OTHER INFORMATION: Primer Vkappa-1g

<400> SEQUENCE: 51
gccatccaga tgacccagtc t                                              21

<210> SEQ ID NO 52
<211> LENGTH: 21
<212> TYPE: DNA
<213> ORGANISM: artificial sequence
<220> FEATURE:
<223> OTHER INFORMATION: Primer Vkappa-2a

<400> SEQUENCE: 52
gatattgtga tgacccagac t                                              21

<210> SEQ ID NO 53
<211> LENGTH: 21
<212> TYPE: DNA
<213> ORGANISM: artificial sequence
<220> FEATURE:
<223> OTHER INFORMATION: Primer Vkappa-2b

<400> SEQUENCE: 53
```

-continued

```
gatgttgtga tgactcagtc t                                              21

<210> SEQ ID NO 54
<211> LENGTH: 21
<212> TYPE: DNA
<213> ORGANISM: artificial sequence
<220> FEATURE:
<223> OTHER INFORMATION: Primer Vkappa-2c

<400> SEQUENCE: 54
gatattgtga tgactcagtc t                                              21

<210> SEQ ID NO 55
<211> LENGTH: 21
<212> TYPE: DNA
<213> ORGANISM: artificial sequence
<220> FEATURE:
<223> OTHER INFORMATION: Primer Vkappa-3a

<400> SEQUENCE: 55
gaaattgtgt tgacgcagtc t                                              21

<210> SEQ ID NO 56
<211> LENGTH: 21
<212> TYPE: DNA
<213> ORGANISM: artificial sequence
<220> FEATURE:
<223> OTHER INFORMATION: Primer Vkappa-3b

<400> SEQUENCE: 56
gaaattgtga tgacgcagtc t                                              21

<210> SEQ ID NO 57
<211> LENGTH: 21
<212> TYPE: DNA
<213> ORGANISM: artificial sequence
<220> FEATURE:
<223> OTHER INFORMATION: Primer Vkappa-3c

<400> SEQUENCE: 57
gaaattgtaa tgacgcagtc t                                              21

<210> SEQ ID NO 58
<211> LENGTH: 21
<212> TYPE: DNA
<213> ORGANISM: artificial sequence
<220> FEATURE:
<223> OTHER INFORMATION: Primer Vkappa-4

<400> SEQUENCE: 58
gacatcgtga tgacccagtc t                                              21

<210> SEQ ID NO 59
<211> LENGTH: 21
<212> TYPE: DNA
<213> ORGANISM: artificial sequence
<220> FEATURE:
<223> OTHER INFORMATION: Primer Vkappa-5

<400> SEQUENCE: 59
gaaacgacac tcacgcagtc t                                              21

<210> SEQ ID NO 60
<211> LENGTH: 21
<212> TYPE: DNA
<213> ORGANISM: artificial sequence
```

-continued

```
<220> FEATURE:
<223> OTHER INFORMATION: Primer Vkappa-6a

<400> SEQUENCE: 60
gaaattgtgc tgactcagtc t                                                21

<210> SEQ ID NO 61
<211> LENGTH: 21
<212> TYPE: DNA
<213> ORGANISM: artificial sequence
<220> FEATURE:
<223> OTHER INFORMATION: Primer Vkappa-6b

<400> SEQUENCE: 61
gatgttgtga tgacacagtc t                                                21

<210> SEQ ID NO 62
<211> LENGTH: 21
<212> TYPE: DNA
<213> ORGANISM: artificial sequence
<220> FEATURE:
<223> OTHER INFORMATION: Primer C-kappa

<400> SEQUENCE: 62
gacagatggt gcagccacag t                                                21

<210> SEQ ID NO 63
<211> LENGTH: 36
<212> TYPE: DNA
<213> ORGANISM: artificial sequence
<220> FEATURE:
<223> OTHER INFORMATION: Primer VH-1a

<400> SEQUENCE: 63
tggacgccca tggcgcaggt gcagctggtg cagtct                                36

<210> SEQ ID NO 64
<211> LENGTH: 36
<212> TYPE: DNA
<213> ORGANISM: artificial sequence
<220> FEATURE:
<223> OTHER INFORMATION: Primer VH-1b

<400> SEQUENCE: 64
tggacgccca tggcgcaggt ccagcttgtg cagtct                                36

<210> SEQ ID NO 65
<211> LENGTH: 36
<212> TYPE: DNA
<213> ORGANISM: artificial sequence
<220> FEATURE:
<223> OTHER INFORMATION: Primer VH-1c

<400> SEQUENCE: 65
tggacgccca tggcgcaggt ccagctggta cagtct                                36

<210> SEQ ID NO 66
<211> LENGTH: 36
<212> TYPE: DNA
<213> ORGANISM: artificial sequence
<220> FEATURE:
<223> OTHER INFORMATION: Primer VH-1c

<400> SEQUENCE: 66
tggacgccca tggcggaggt ccagctggta cagtct                                36
```

<210> SEQ ID NO 67
<211> LENGTH: 36
<212> TYPE: DNA
<213> ORGANISM: artificial sequence
<220> FEATURE:
<223> OTHER INFORMATION: Primer VH-1e

<400> SEQUENCE: 67
tggacgccca tggcgcagat gcagctggta cagtct					36

<210> SEQ ID NO 68
<211> LENGTH: 36
<212> TYPE: DNA
<213> ORGANISM: artificial sequence
<220> FEATURE:
<223> OTHER INFORMATION: Primer VH-2a

<400> SEQUENCE: 68
tggacgccca tggcgcagat caccttgaag gagtct					36

<210> SEQ ID NO 69
<211> LENGTH: 36
<212> TYPE: DNA
<213> ORGANISM: artificial sequence
<220> FEATURE:
<223> OTHER INFORMATION: Primer VH-2b

<400> SEQUENCE: 69
tggacgccca tggcgcaggt caccttgaag gagtct					36

<210> SEQ ID NO 70
<211> LENGTH: 36
<212> TYPE: DNA
<213> ORGANISM: artificial sequence
<220> FEATURE:
<223> OTHER INFORMATION: Primer VH-3a

<400> SEQUENCE: 70
tggacgccca tggcggaagt gcagctggtg gagtct					36

<210> SEQ ID NO 71
<211> LENGTH: 36
<212> TYPE: DNA
<213> ORGANISM: artificial sequence
<220> FEATURE:
<223> OTHER INFORMATION: Primer VH-3b

<400> SEQUENCE: 71
tggacgccca tggcgcaggt gcagctggtg gagtct					36

<210> SEQ ID NO 72
<211> LENGTH: 36
<212> TYPE: DNA
<213> ORGANISM: artificial sequence
<220> FEATURE:
<223> OTHER INFORMATION: Primer VH-3c

<400> SEQUENCE: 72
tggacgccca tggcggaggt gcagctgttg gagtct					36

<210> SEQ ID NO 73
<211> LENGTH: 36
<212> TYPE: DNA
<213> ORGANISM: artificial sequence
<220> FEATURE:
<223> OTHER INFORMATION: Primer VH-4a

<400> SEQUENCE: 73
tggacgccca tggcgcaggt gcagctgcag gagtcg          36

<210> SEQ ID NO 74
<211> LENGTH: 36
<212> TYPE: DNA
<213> ORGANISM: artificial sequence
<220> FEATURE:
<223> OTHER INFORMATION: Primer VH-4b

<400> SEQUENCE: 74
tggacgccca tggcgcagct gcagctgcag gagtcg          36

<210> SEQ ID NO 75
<211> LENGTH: 36
<212> TYPE: DNA
<213> ORGANISM: artificial sequence
<220> FEATURE:
<223> OTHER INFORMATION: Primer VH-4c

<400> SEQUENCE: 75
tggacgccca tggcgcaggt gcagctacag cagtgg          36

<210> SEQ ID NO 76
<211> LENGTH: 36
<212> TYPE: DNA
<213> ORGANISM: artificial sequence
<220> FEATURE:
<223> OTHER INFORMATION: Primer VH-5

<400> SEQUENCE: 76
tggacgccca tggcggaagt gcagctggtg cagtct          36

<210> SEQ ID NO 77
<211> LENGTH: 36
<212> TYPE: DNA
<213> ORGANISM: artificial sequence
<220> FEATURE:
<223> OTHER INFORMATION: Primer VH-6

<400> SEQUENCE: 77
tggacgccca tggcgcaggt acagctgcag cagtca          36

<210> SEQ ID NO 78
<211> LENGTH: 36
<212> TYPE: DNA
<213> ORGANISM: artificial sequence
<220> FEATURE:
<223> OTHER INFORMATION: Primer VH-7

<400> SEQUENCE: 78
tggacgccca tggcgcaggt gcagctggtg caatct          36

<210> SEQ ID NO 79
<211> LENGTH: 33
<212> TYPE: DNA
<213> ORGANISM: artificial sequence
<220> FEATURE:
<223> OTHER INFORMATION: Primer IgM

<400> SEQUENCE: 79
tgggaaaagc ttaagggttg gggcggatgc act          33

<210> SEQ ID NO 80
<211> LENGTH: 36
<212> TYPE: DNA
<213> ORGANISM: artificial sequence

```
<220> FEATURE:
<223> OTHER INFORMATION: Primer Vlambda-1a

<400> SEQUENCE: 80
cctacagaac gcgtacagtc tgtgctgacg cagcca                              36

<210> SEQ ID NO 81
<211> LENGTH: 36
<212> TYPE: DNA
<213> ORGANISM: artificial sequence
<220> FEATURE:
<223> OTHER INFORMATION: Primer Vlambda-1b

<400> SEQUENCE: 81
cctacagaac gcgtacagtc tgtgctgacg cagccg                              36

<210> SEQ ID NO 82
<211> LENGTH: 36
<212> TYPE: DNA
<213> ORGANISM: artificial sequence
<220> FEATURE:
<223> OTHER INFORMATION: Primer Vlambda-3a

<400> SEQUENCE: 82
cctacagaac gcgtacagtc tgccctgact cagcct                              36

<210> SEQ ID NO 83
<211> LENGTH: 36
<212> TYPE: DNA
<213> ORGANISM: artificial sequence
<220> FEATURE:
<223> OTHER INFORMATION: Primer Vlambda-3a

<400> SEQUENCE: 83
cctacagaac gcgtatccta tgagctgaca cagcca                              36

<210> SEQ ID NO 84
<211> LENGTH: 36
<212> TYPE: DNA
<213> ORGANISM: artificial sequence
<220> FEATURE:
<223> OTHER INFORMATION: Primer Vlambda-3b

<400> SEQUENCE: 84
cctacagaac gcgtatcctc tgagctgaca caggac                              36

<210> SEQ ID NO 85
<211> LENGTH: 36
<212> TYPE: DNA
<213> ORGANISM: artificial sequence
<220> FEATURE:
<223> OTHER INFORMATION: Primer Vlambda-3c

<400> SEQUENCE: 85
cctacagaac gcgtatccta tgtgctgaca cagcca                              36

<210> SEQ ID NO 86
<211> LENGTH: 36
<212> TYPE: DNA
<213> ORGANISM: artificial sequence
<220> FEATURE:
<223> OTHER INFORMATION: Primer Vlambda-3c

<400> SEQUENCE: 86
cctacagaac gcgtatccta tgagctgaca cagcta                              36
```

```
<210> SEQ ID NO 87
<211> LENGTH: 36
<212> TYPE: DNA
<213> ORGANISM: artificial sequence
<220> FEATURE:
<223> OTHER INFORMATION: Primer Vlambda-3e

<400> SEQUENCE: 87
cctacagaac gcgtatccta tgagctgatg cagcca                              36

<210> SEQ ID NO 88
<211> LENGTH: 36
<212> TYPE: DNA
<213> ORGANISM: artificial sequence
<220> FEATURE:
<223> OTHER INFORMATION: Primer Vlambda-4a

<400> SEQUENCE: 88
cctacagaac gcgtactgcc tgtgctgact cagccc                              36

<210> SEQ ID NO 89
<211> LENGTH: 36
<212> TYPE: DNA
<213> ORGANISM: artificial sequence
<220> FEATURE:
<223> OTHER INFORMATION: Primer Vlambda-4b

<400> SEQUENCE: 89
cctacagaac gcgtacagcc tgtgctgact caatca                              36

<210> SEQ ID NO 90
<211> LENGTH: 36
<212> TYPE: DNA
<213> ORGANISM: artificial sequence
<220> FEATURE:
<223> OTHER INFORMATION: Primer Vlambda-4c

<400> SEQUENCE: 90
cctacagaac gcgtacagct tgtgctgact caatcg                              36

<210> SEQ ID NO 91
<211> LENGTH: 36
<212> TYPE: DNA
<213> ORGANISM: artificial sequence
<220> FEATURE:
<223> OTHER INFORMATION: Primer Vlambda-5a

<400> SEQUENCE: 91
cctacagaac gcgtacagcc tgtgctgact cagcca                              36

<210> SEQ ID NO 92
<211> LENGTH: 36
<212> TYPE: DNA
<213> ORGANISM: artificial sequence
<220> FEATURE:
<223> OTHER INFORMATION: Primer Vlambda-5b

<400> SEQUENCE: 92
cctacagaac gcgtacaggc tgtgctgact cagccg                              36

<210> SEQ ID NO 93
<211> LENGTH: 36
<212> TYPE: DNA
<213> ORGANISM: artificial sequence
<220> FEATURE:
<223> OTHER INFORMATION: Primer Vlambda-6

<400> SEQUENCE: 93
```
cctacagaac gcgtaaattt tatgctgact cagccc        36

<210> SEQ ID NO 94
<211> LENGTH: 36
<212> TYPE: DNA
<213> ORGANISM: artificial sequence
<220> FEATURE:
<223> OTHER INFORMATION: Primer Vlambda-7a

<400> SEQUENCE: 94
cctacagaac gcgtacagac tgtggtgact caggag        36

<210> SEQ ID NO 95
<211> LENGTH: 36
<212> TYPE: DNA
<213> ORGANISM: artificial sequence
<220> FEATURE:
<223> OTHER INFORMATION: Primer Vlambda-7b

<400> SEQUENCE: 95
cctacagaac gcgtacaggc tgtggtgact caggag        36

<210> SEQ ID NO 96
<211> LENGTH: 36
<212> TYPE: DNA
<213> ORGANISM: artificial sequence
<220> FEATURE:
<223> OTHER INFORMATION: Primer Vlambda-8

<400> SEQUENCE: 96
cctacagaac gcgtacagac tgtggtgacc caggag        36

<210> SEQ ID NO 97
<211> LENGTH: 36
<212> TYPE: DNA
<213> ORGANISM: artificial sequence
<220> FEATURE:
<223> OTHER INFORMATION: Primer Vlambda-9

<400> SEQUENCE: 97
cctacagaac gcgtacagcc tgtgctgact cagcca        36

<210> SEQ ID NO 98
<211> LENGTH: 36
<212> TYPE: DNA
<213> ORGANISM: artificial sequence
<220> FEATURE:
<223> OTHER INFORMATION: Primer Vlambda-10

<400> SEQUENCE: 98
cctacagaac gcgtacaggc agggctgact cagcca        36

<210> SEQ ID NO 99
<211> LENGTH: 39
<212> TYPE: DNA
<213> ORGANISM: artificial sequence
<220> FEATURE:
<223> OTHER INFORMATION: Primer C-lambda

<400> SEQUENCE: 99
gggcggcagg gcggccgcgg acggcgggaa cagagtgac     39

<210> SEQ ID NO 100
<211> LENGTH: 36
<212> TYPE: DNA
<213> ORGANISM: artificial sequence -continued
<220> FEATURE:
<223> OTHER INFORMATION: Primer Vkappa-1a

<400> SEQUENCE: 100
cctacagaac gcgtagacat ccagatgacc cagtct                                    36

<210> SEQ ID NO 101
<211> LENGTH: 36
<212> TYPE: DNA
<213> ORGANISM: artificial sequence
<220> FEATURE:
<223> OTHER INFORMATION: Primer Vkappa-1b

<400> SEQUENCE: 101
cctacagaac gcgtaaacat ccagatgacc cagtct                                    36

<210> SEQ ID NO 102
<211> LENGTH: 36
<212> TYPE: DNA
<213> ORGANISM: artificial sequence
<220> FEATURE:
<223> OTHER INFORMATION: Primer Vkappa-1c

<400> SEQUENCE: 102
cctacagaac gcgtagccat ccagttgacc cagtct                                    36

<210> SEQ ID NO 103
<211> LENGTH: 36
<212> TYPE: DNA
<213> ORGANISM: artificial sequence
<220> FEATURE:
<223> OTHER INFORMATION: Primer Vkappa-1d

<400> SEQUENCE: 103
cctacagaac gcgtagacat ccagttgacc cagtct                                    36

<210> SEQ ID NO 104
<211> LENGTH: 36
<212> TYPE: DNA
<213> ORGANISM: artificial sequence
<220> FEATURE:
<223> OTHER INFORMATION: Primer Vkappa-1e

<400> SEQUENCE: 104
cctacagaac gcgtagccat ccggatgacc cagtct                                    36

<210> SEQ ID NO 105
<211> LENGTH: 36
<212> TYPE: DNA
<213> ORGANISM: artificial sequence
<220> FEATURE:
<223> OTHER INFORMATION: Primer Vkappa-1f

<400> SEQUENCE: 105
cctacagaac gcgtagtcat ctggatgacc cagtct                                    36

<210> SEQ ID NO 106
<211> LENGTH: 36
<212> TYPE: DNA
<213> ORGANISM: artificial sequence
<220> FEATURE:
<223> OTHER INFORMATION: Primer Vkappa-1g

<400> SEQUENCE: 106
cctacagaac gcgtagccat ccagatgacc cagtct                                    36

```
<210> SEQ ID NO 107
<211> LENGTH: 36
<212> TYPE: DNA
<213> ORGANISM: artificial sequence
<220> FEATURE:
<223> OTHER INFORMATION: Primer Vkappa-2a

<400> SEQUENCE: 107
cctacagaac gcgtagatat tgtgatgacc cagact                    36

<210> SEQ ID NO 108
<211> LENGTH: 36
<212> TYPE: DNA
<213> ORGANISM: artificial sequence
<220> FEATURE:
<223> OTHER INFORMATION: Primer Vkappa-2b

<400> SEQUENCE: 108
cctacagaac gcgtagatgt tgtgatgact cagtct                    36

<210> SEQ ID NO 109
<211> LENGTH: 36
<212> TYPE: DNA
<213> ORGANISM: artificial sequence
<220> FEATURE:
<223> OTHER INFORMATION: Primer Vkappa-2c

<400> SEQUENCE: 109
cctacagaac gcgtagatat tgtgatgact cagtct                    36

<210> SEQ ID NO 110
<211> LENGTH: 36
<212> TYPE: DNA
<213> ORGANISM: artificial sequence
<220> FEATURE:
<223> OTHER INFORMATION: Primer Vkappa-3a

<400> SEQUENCE: 110
cctacagaac gcgtagaaat tgtgttgacg cagtct                    36

<210> SEQ ID NO 111
<211> LENGTH: 36
<212> TYPE: DNA
<213> ORGANISM: artificial sequence
<220> FEATURE:
<223> OTHER INFORMATION: Primer Vkappa-3b

<400> SEQUENCE: 111
cctacagaac gcgtagaaat tgtgatgacg cagtct                    36

<210> SEQ ID NO 112
<211> LENGTH: 36
<212> TYPE: DNA
<213> ORGANISM: artificial sequence
<220> FEATURE:
<223> OTHER INFORMATION: Primer Vkappa-3c

<400> SEQUENCE: 112
cctacagaac gcgtagaaat tgtaatgacg cagtct                    36

<210> SEQ ID NO 113
<211> LENGTH: 36
<212> TYPE: DNA
<213> ORGANISM: artificial sequence
<220> FEATURE:
<223> OTHER INFORMATION: Primer Vkappa-4

<400> SEQUENCE: 113
```
cctacagaac gcgtagacat cgtgatgacc cagtct          36

<210> SEQ ID NO 114
<211> LENGTH: 36
<212> TYPE: DNA
<213> ORGANISM: artificial sequence
<220> FEATURE:
<223> OTHER INFORMATION: Primer Vkappa-5

<400> SEQUENCE: 114
cctacagaac gcgtagaaac gacactcacg cagtct          36

<210> SEQ ID NO 115
<211> LENGTH: 36
<212> TYPE: DNA
<213> ORGANISM: artificial sequence
<220> FEATURE:
<223> OTHER INFORMATION: Primer Vkappa-6a

<400> SEQUENCE: 115
cctacagaac gcgtagaaat tgtgctgact cagtct          36

<210> SEQ ID NO 116
<211> LENGTH: 36
<212> TYPE: DNA
<213> ORGANISM: artificial sequence
<220> FEATURE:
<223> OTHER INFORMATION: Primer Vkappa-6b

<400> SEQUENCE: 116
cctacagaac gcgtagatgt tgtgatgaca cagtct          36

<210> SEQ ID NO 117
<211> LENGTH: 39
<212> TYPE: DNA
<213> ORGANISM: artificial sequence
<220> FEATURE:
<223> OTHER INFORMATION: Primer C-kappa

<400> SEQUENCE: 117
gggcggcagg gcggccgcga cagatggtgc agccacagt          39

<210> SEQ ID NO 118
<211> LENGTH: 24
<212> TYPE: PRT
<213> ORGANISM: artificial sequence
<220> FEATURE:
<223> OTHER INFORMATION: synthetic VL

<400> SEQUENCE: 118

Asp Glu Ala Asp Tyr Tyr Cys Asn Ser Arg Asp Arg Ser Gly Asn His
1               5                   10                  15

Val Asn Val Leu Phe Gly Gly Gly
            20

<210> SEQ ID NO 119
<211> LENGTH: 22
<212> TYPE: PRT
<213> ORGANISM: artificial sequence
<220> FEATURE:
<223> OTHER INFORMATION: synthetic VL

<400> SEQUENCE: 119

Asp Glu Ala Asp Tyr Tyr Cys Asn Ser Arg Ala Asp Ser Ala Arg Arg
1               5                   10                  15

Val Leu Phe Gly Gly Gly
            20

<210> SEQ ID NO 120
<211> LENGTH: 22
<212> TYPE: PRT
<213> ORGANISM: artificial sequence
<220> FEATURE:
<223> OTHER INFORMATION: synthetic VL

<400> SEQUENCE: 120

Asp Glu Ala Asp Tyr Tyr Cys Asn Ser Arg Asp Ser Ser Ala Arg Arg
1               5                   10                  15

Val Leu Phe Gly Gly Gly
            20

<210> SEQ ID NO 121
<211> LENGTH: 22
<212> TYPE: PRT
<213> ORGANISM: artificial sequence
<220> FEATURE:
<223> OTHER INFORMATION: synthetic VL

<400> SEQUENCE: 121

Asp Glu Ala Asp Tyr Tyr Cys Ser Ser Arg Asp Ser Ser Thr Lys Gln
1               5                   10                  15

Val Leu Phe Gly Gly Gly
            20

<210> SEQ ID NO 122
<211> LENGTH: 22
<212> TYPE: PRT
<213> ORGANISM: artificial sequence
<220> FEATURE:
<223> OTHER INFORMATION: synthetic VL

<400> SEQUENCE: 122

Asp Glu Ala Asp Tyr Tyr Cys Asn Ser Arg Glu Asn Asn Arg Tyr Ser
1               5                   10                  15

Val Leu Phe Gly Gly Gly
            20

<210> SEQ ID NO 123
<211> LENGTH: 22
<212> TYPE: PRT
<213> ORGANISM: artificial sequence
<220> FEATURE:
<223> OTHER INFORMATION: synthetic VL

<400> SEQUENCE: 123

Asp Glu Ala Asp Tyr Tyr Cys Asn Ser Arg Thr Asp Pro Pro Lys
1               5                   10                  15

Val Leu Phe Gly Gly Gly
            20

<210> SEQ ID NO 124
<211> LENGTH: 22
<212> TYPE: PRT
<213> ORGANISM: artificial sequence
<220> FEATURE:
<223> OTHER INFORMATION: synthetic VL

<400> SEQUENCE: 124

Asp Glu Ala Asp Tyr Tyr Cys Asn Ser Arg Asn Ser Thr Lys Arg Ser
1               5                   10                  15

```
Val Leu Phe Gly Gly Gly
            20

<210> SEQ ID NO 125
<211> LENGTH: 22
<212> TYPE: PRT
<213> ORGANISM: artificial sequence
<220> FEATURE:
<223> OTHER INFORMATION: synthetic VL

<400> SEQUENCE: 125

Asp Glu Ala Asp Tyr Tyr Cys Asn Ser Arg Arg Thr His Pro Lys Met
1               5                   10                  15

Val Leu Phe Gly Gly Gly
            20
```

USE OF AN ANTIBODY AGAINST THE LAMININ RECEPTOR OR LAMININ RECEPTOR PRECURSOR FOR THE TREATMENT OR DIAGNOSIS OF SEVERAL CANCER TYPES

This application is a National Stage of International Application PCT/EP2006/003104, filed Apr. 5, 2006, published Oct. 12, 2006, which claims the priority of European Application No. 05 007 380.8, filed Apr. 5, 2005.

The present invention relates to the use of a recombinant antibody comprising a binding site specific for an epitope of the laminin receptor or laminin receptor precursor for treatment or diagnosis of several cancer types. Preferably, this antibody additionally comprises a binding site for at least one particular cell surface antigen.

Originally, the 67 kDa laminin receptor (LR) was isolated from tumor cells. This mature receptor shows high affinity to laminin, belongs to the integrin family and putatively acts as an auxiliary molecule involved in regulating and stabilizing the interaction of laminin with the bona fide laminin receptor (Ardini et al., Mol. Biol. Evol. 15(8) (1998), 1017-25).

Screening of a human cDNA expression library using an antibody against the purified 67 kDa protein led to the isolation of the full length cDNA encoding the protein with a calculated molecular mass of 32 kDa (Rao et al., Biochemistry 28 (1989), 7476-86). In vitro translation of the mRNA yielded a protein with an apparent molecular mass of 37 kDa determined by SDS-polyacrylamide gel electrophoresis. The mechanisms through which the 37 kDa monomeric precursor (LRP) is processed to the mature 67 kDa LR is not clear, but homo-dimerization of 37 kDa monomeric LRP after acylation by fatty acids appears to be the most probable (Landowski et al., Biochemistry 5; 34(35), (1995), 11276-87).

Experimental studies indicate that the 37 kDa LRP/67 kDa LR acts as a receptor for the uptake of the prion protein into eukaryotic cells and is involved in the entry of the Sindbis Virus. The 37 kDa form also occurs in the cytosol where it is associated with the ribosome. A possible relationship between the ribosomal protein p40 and a laminin-binding protein was suggested by the fact that it contains an octapeptide sequence identical to that of a peptide derived from the 67 kDa laminin receptor. Sequence analysis revealed that the 37 kDa LRP cDNA is virtually identical to the cDNA encoding the mouse protein p40. Further evidence suggests that the 37 kDa LRP/p40 protein is a component of the translational machinery, being specifically associated with the 40S ribosomal subunit. It seems to be that initially the ribosomal protein was not able to bind laminin. During evolution concurrent with the appearance of the extra-cellular matrix, palindromic sequences were acquired which apparently conferred laminin binding capabilities to the molecule. A 20-amino acid synthetic peptide, designated as a peptide G, derived from the 37 kDa LRP and containing the palindromic sequence LMW-WML (SEQ ID NO: 1) was found to be responsible for binding to laminin (Castronovo et al., Biochem. Biophys. Res. Commun. 177 (1991), 177-83).

The 37 kDa/67 kDa laminin receptor is encoded by several genes in the genome of mammals. 6 gene copies in the murine genome and 26 copies in humans were identified. Most of these copies are considered to be pseudogenes. There is evidence that at least two copies are active in the murine genome. The laminin receptor is highly conserved among vertebrates. Only 1.7% average sequence divergence between chicken and mammalian proteins was observed (Ardini et al., 1998; Rao et al. 1989). The amino acid sequence of the human gene product differs from the murine counterpart only in four amino acids.

While the mature 67 kDa LR is expressed on the surface of many normal cells as well as on tumor cells, there appears to be a preferential expression of the 37 kDa LRP on fetal and tumor cells (Rohrer et al., Mod. Asp. Immunobiol. 1(5) (2001), 191-5. Absorption ELISA and flow cytometry shows that carcinomas of the colon, lung, gastric mucosa, larynx, pharynx, breast and kidney are positive for LRP while normal tissue of the same type is negative. Screening the expression of the LRP on various hematological malignancies and healthy hematopoetic cells revealed a significant expression of the receptor on the tumor cells, whereas no LRP was present on respective cells isolated from healthy individuals.

The high affinity 67 kDa mature LR was shown to be expressed at high levels on lung carcinoma, breast carcinoma and several other invasive solid tumors and its expression level correlates with metastatic phenotype of the tumor. In contrast, it is expressed at relatively low levels in benign and normal tissues. Breast carcinoma patients with tumors expressing both laminin and its receptor showed poor survival prognosis in comparison with patients with LRP-negative tumors. The primary function of the membrane receptor is to stabilize the binding of laminin to cell surface integrins, acting as an integrin accessory molecule. Anti-idiotypic antibodies carrying the internal image of the LR-binding peptide YIGSR inhibit spontaneous metastasis in an in vivo lung carcinoma mouse model (Koliakos et al., In Vivo (16(6) (2002), 511-8). Since the adhesion to the basement membrane is considered to be a critical step in the metastatic cascade, the laminin-binding function of this protein makes it a potential target for therapeutic intervention in metastatic disease as well as a useful prognostic factor (Narumi et al., Jpn J Cancer Res., 90(4), 425-431). However, so far the knowledge of other kinds of cancers showing high LR receptor expression and the availability of means suitable for specific treatment is limited.

Thus, the technical problem underlying the present invention was to provide means suitable for specific treatment of cancer associated with high LR expression.

The solution of the said technical problem is achieved by providing the embodiments characterized in the claims.

Antibodies (e.g., scFv S18, S18 5-4-1 and N3) have been selected that are highly specific for the laminin receptor or its precursor and, thus, useful for therapy and diagnosis of cancers showing high LR expression, e.g. B-cell chronic lymphatic leukaemia (B-CLL). It could be shown that these antibodies bind to peripheral blood lymphocytes (PBL) from patients with B-cell chronic leukaemia (B-CLL) but not to enriched B-cell populations from healthy donors.

The antibodies of the present invention are also suitable to treat and diagnose the following types of cancer: non-Hodgkin's lymphoma, Hodgkin's lymphoma, lung cancer, colon carcinoma, mammary carcinoma, pancreatic carcinoma, prostate cancer, metastasising cancers, minimal residual disease.

50 µL crude periplasmic extracts from each of the 48 individual clones were incubated for 2 hours at room temperature followed by an anti-Penta His HRP-conjugate (Qiagen, Hilden, Germany) (1 µg/mL). As HRP-substrate, 50 µL of TMB (KPL) were used. After stopping the reaction with 50 µL 0.5 M $H_2SO_4$, absorbance at 450 nm was measured.

Figure 2:
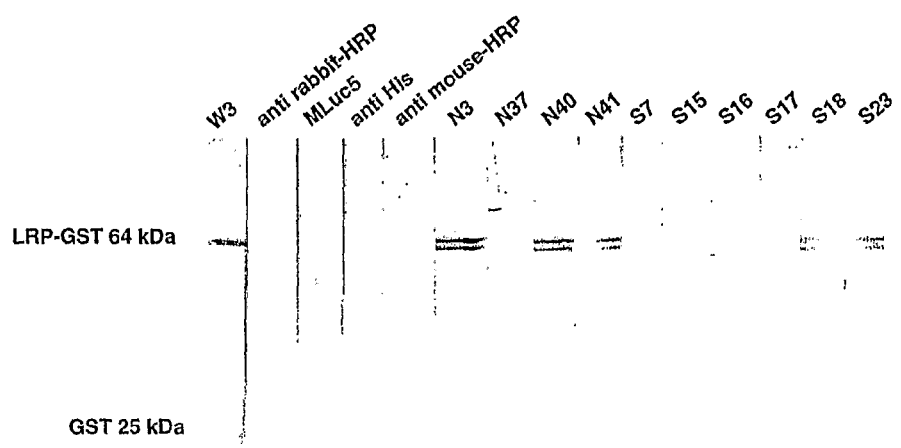

FIG. 2: Detection of recombinant human LRP in Western Blot

In each lane a mixture of GST and LRP-GST fusion protein was separated by SDS-PAGE and transferred onto a nitrocellulose membrane. The Blot was cut into single strips and incubated with crude periplasmic extracts (1:5 diluted) from the individual scFvs or control antibodies. The polyclonal anti-LRP-GST rabbit serum W3 (1.3 µg/mL) was detected with HRP-conjugated polyclonal goat anti-rabbit IgG antibodies (Dianova Hamburg, Germany, 0.2 µg/mL). The bound scFvs were detected with a mouse anti-penta histidine mAb (Qiagen, 1 µg/mL) followed by the HRP-conjugated goat anti-mouse IgG antibodies (Dianova, 0.5 µg/mL). Controls: anti-His, mouse anti-histidine mAb followed by HRP-conjugated goat anti-mouse IgG antibodies; anti-mouse-HRP, HRP-conjugated goat anti-mouse IgG antibodies alone; MLuC5, commercial anti-LRP mAb not suitable for Western Blot analysis.

Figure 3:
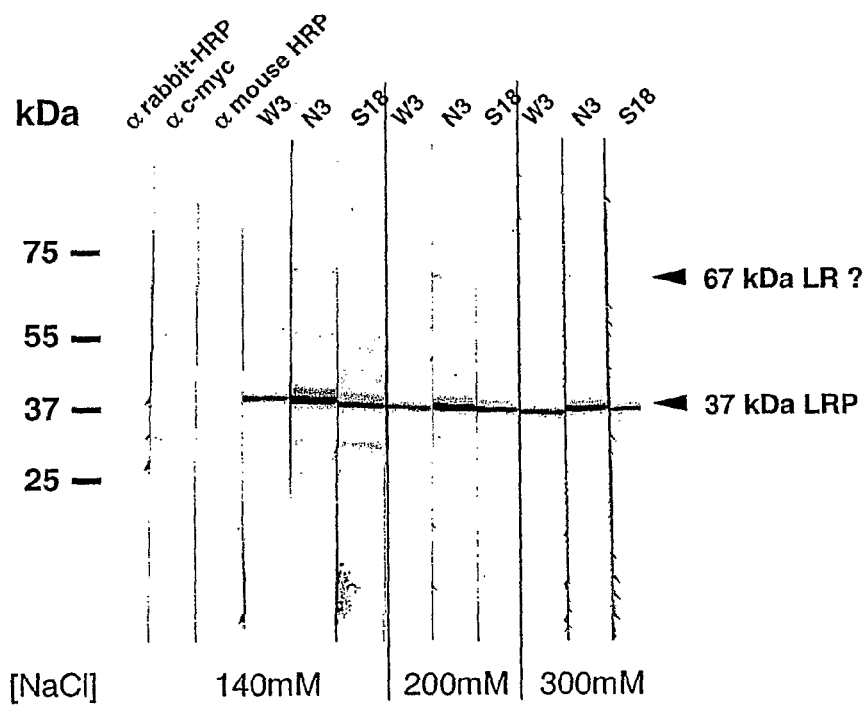

FIG. 3: Detection of LRP/LR from N2a lysates in Western Blot by IMAC purified scFvs N3 and S18

In each lane, total cell-lysates were separated by SDS-PAGE and transferred to a nitrocellulose membrane. The blot was cut into single strips and incubated with the respective scFvs (1.5 µg/mL) or with controls at indicated salt concentrations. The polyclonal anti-LRP-GST rabbit serum W3 (1.3 µg/mL) was detected with a HRP-conjugated polyclonal goat anti-rabbit IgG antibodies (Dianova, 0.2 µg/mL). The bound scFvs were detected with the anti-c-myc mouse mAb 9E10 (a kind gift of Dr. Moldenhauer, DKFZ Heidelberg, 0.5 µg/mL) followed by the HRP-conjugated goat anti-mouse IgG antibodies (Dianova, 0.5 µg/mL). Controls: anti-rabbit-HRP, HRP-conjugated goat anti-rabbit IgG antibodies alone; anti-c-myc, anti-c-myc mouse mAb 9E10 followed by the HRP-conjugated goat anti-mouse IgG antibodies; anti mouse-HRP, HRP-conjugated goat anti-mouse IgG antibodies alone.

Figure 4:
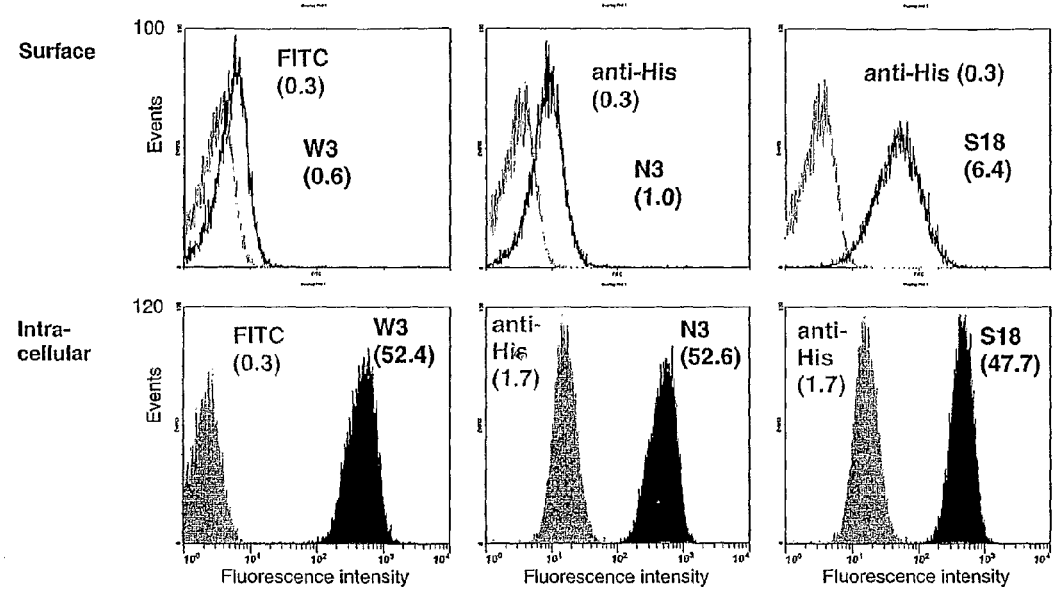
Figure 4:
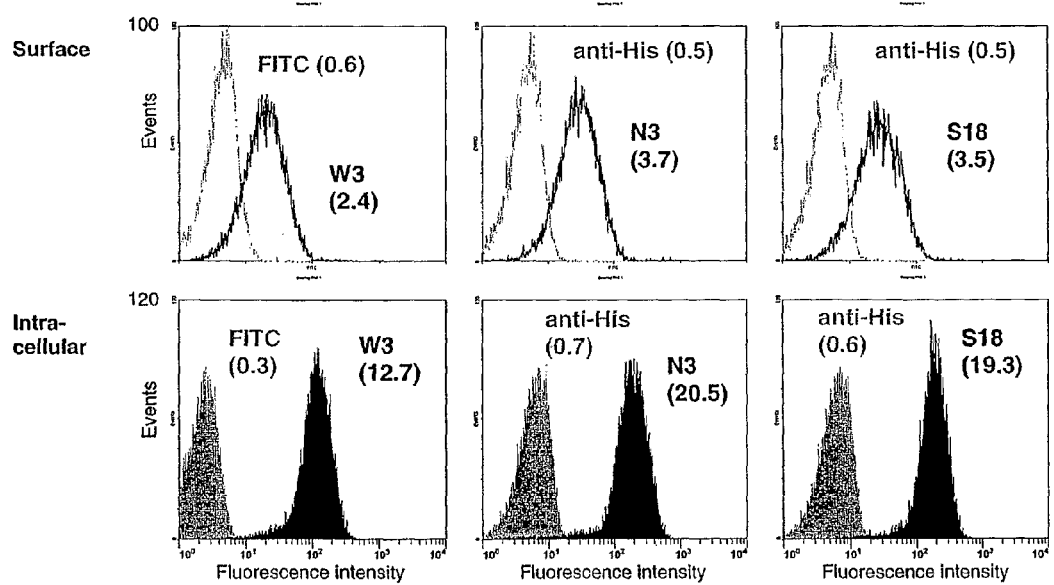

FIG. 4: Flow cytometric analysis of the anti-LR/LRP scFvs N3 and S18 binding to N2a and Jurkat cells The indicated cell lines were stained with 100 µg/mL rabbit serum W3 followed by FITC-conjugated goat anti-rabbit IgG antibodies (15 µg/mL). The human scFv N3 and S18 were used at concentration of 18 µg/mL and were detected with anti-His mAb (10 µg/mL) followed by 15 µg/mL FITC-conjugated goat anti-mouse IgG antibodies. Controls: FITC, cell staining with FITC-conjugated goat anti-rabbit IgG antibodies alone; anti-His, cell staining with anti-His mAb followed by FITC-conjugated goat anti-mouse IgG antibodies. The gray histograms represent cell stainings with the corresponding secondary reagent alone. Observed mean fluorescence intensities are indicated in the brackets.

FIG. 5: Flow cytometric analysis of the scFv variants N3 and S18 binding to enriched B-lymphocytes from healthy donors and to PBMC from B-CLL patients (a) PBMC from three different patients (Binet stage A-C) with B-CLL were isolated from the peripheral blood. $1 \times 10^6$ cells were used for staining with either anti-human CD19 mAb HD37 (10 µg/mL) followed by FITC-conjugated goat anti-mouse IgG antibodies (15 µg/mL) or with anti-LRP-GST rabbit serum W3 (20 µg/mL) followed by FITC-conjugated goat anti-rabbit IgG antibodies (15 µg/mL). The human scFvs N3 and S18 were used at a concentration of 50 µg/mL and were detected with anti-His mAb (10 µg/mL) followed by FITC-conjugated goat anti-mouse IgG antibodies (15 µg/mL). The gray histograms represent cell stainings with the corresponding secondary reagent alone. (b) The B lymphocytes were enriched by negative selection from PBMC of 4 healthy volunteers. $3 \times 10^5$ enriched B cells were used for one staining performed as described for (a).

FIGS. 6a and 6b: Amino acid sequence of $V_H$ and $V_L$ of the scFv N3 (a) and S18 (b)

The positions of CDR1, CDR2 and CDR3 are indicated.

FIG. 7: Alignment of the CDR3 region of clones containing a synthetic $V_L$.

Upper line shows the amino acid sequence of the parental clone S18. Permutated positions in the newly isolated fragments are underlined. Identical amino acids are highlighted grey.

Figure 8:
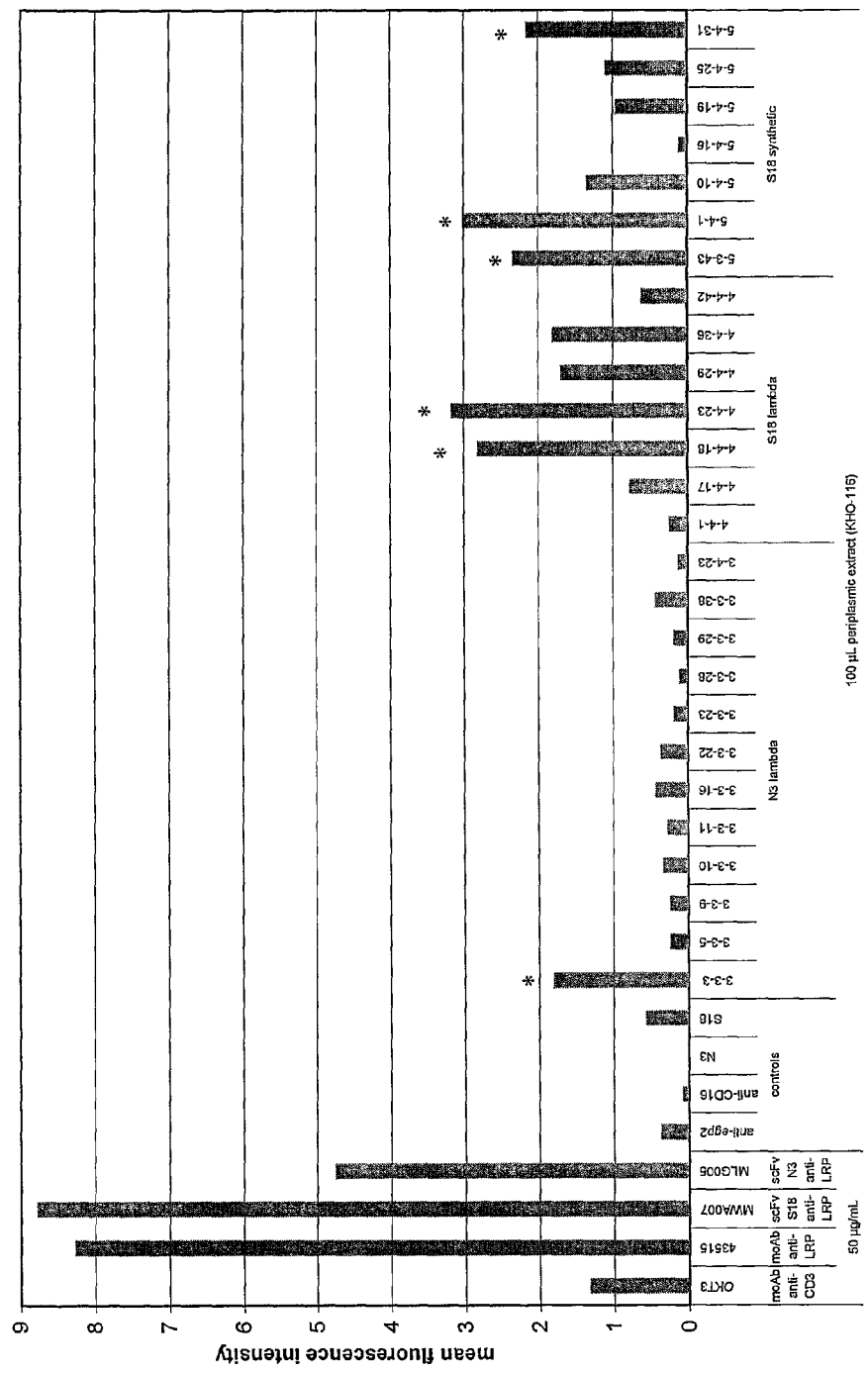

FIG. 8: Testing crude periplasmic extracts of affinity-matured anti-LRP scFv on HEK 293 cells.

$10^6$ HEK 293 cells were stained with 100 µL periplasmic extract or 50 µg/mL purified S18 or N3 followed by 10 µg/mL moAb anti-$(His)_6$ and 15 µg/mL FITC-conjugated goat anti-mIgG. Control antibodies OKT3 anti-CD3 and anti-LRP 43515 were detected with 15 µg/mL FITC-conjugated goat anti-mIgG. $10^4$ living cells were analysed using a Beckman-Coulter flow cytometer after exclusion of dead cells by propidium iodide staining. Background fluorescence values from the control staining of the cells with the secondary reagents alone were subtracted and mean fluorescence intensities from the specific staining were plotted in the diagram. Clones selected for further characterisation are marked by asterisks.

Figure 9:
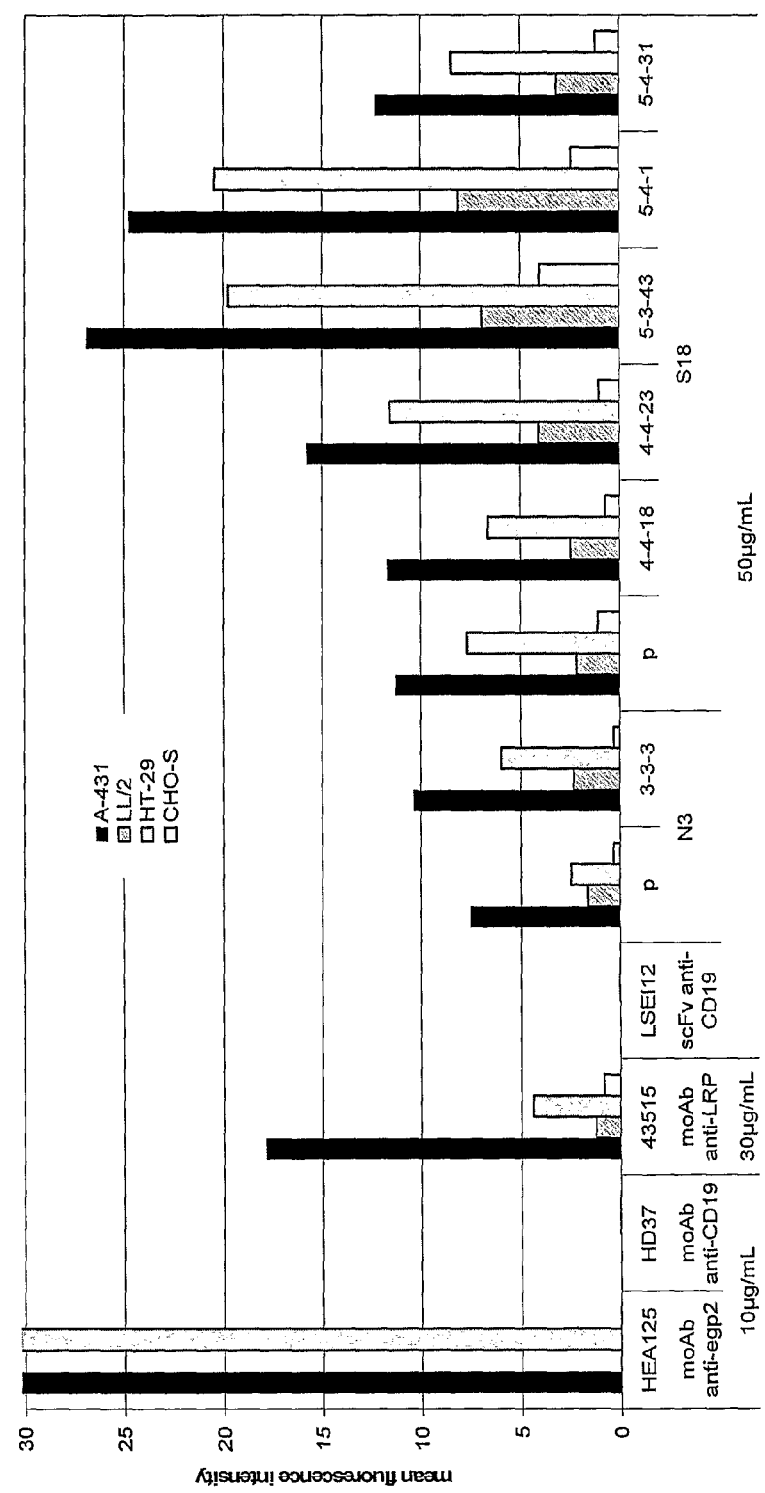

FIG. 9: Test of affinity-improved human anti-LRP scFv on different cell lines.

$10^6$ cells of the indicated cell lines were stained with 50 µg/mL of the indicated scFv followed by 10 µg/mL moAb anti-c-myc 9E10 and 15 µg/mL FITC-conj. goat anti-mIgG. The monoclonal antibodies anti-egp-2 HEA125 (10 µg/mL), anti-CD19 HD37 (10 µg/mL) and anti-LRP 43515 (30 µg/mL) were detected by 15 µg/mL FITC-conj. goat anti-mIgG. $10^4$ living cells were analysed using a Beckman-Coulter flow cytometer after exclusion of dead cells by propidium iodide staining. Background fluorescence values from the control stainings of the cells with the secondary reagents alone were subtracted and mean fluorescence intensities from the specific stainings were plotted in the diagram.

Figure 10:
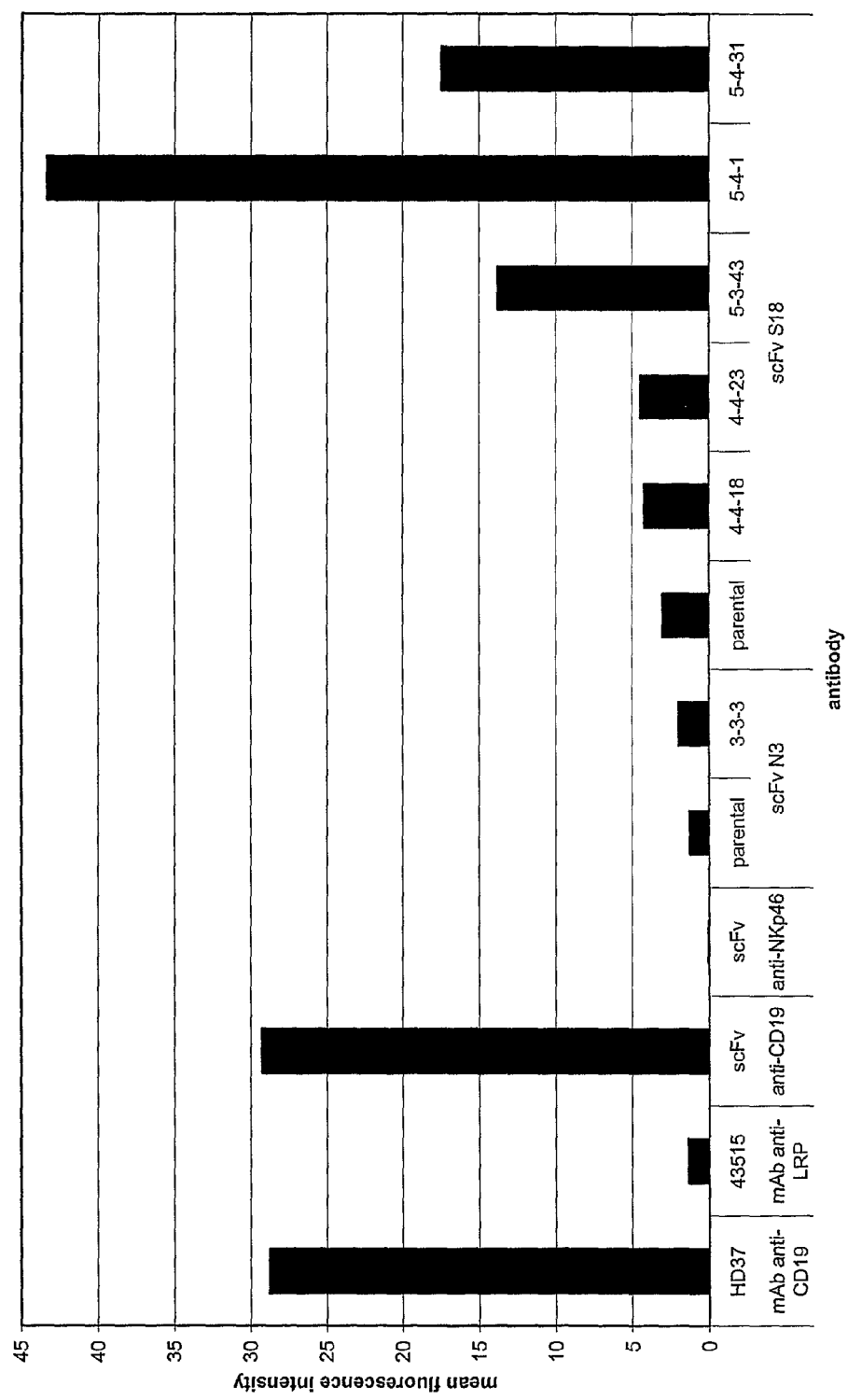

FIG. 10: Flow cytometric analysis of the chain-shuffled anti-LRP scFv variants binding to PBMC from B-CLL patients PBMC from a patient with B cell-chronic lymphocytic leukaemia (B-CLL) in Binet stage C were isolated from heparinized peripheral blood. $5 \times 10^5$ cells were used for staining with either anti-human CD19 mAb HD37 or with anti-LRP mAb 43515 (50 µg/mL) followed by FITC-conjugated goat anti-mouse IgG antibodies (15 µg/mL). The scFvs were used at a concentration of 50 µg/mL and were detected with anti-His mAb 13/45/31-2 (10 µg/mL) followed by FITC-conjugated goat anti-mouse IgG antibodies (15 µg/mL). After flow cytometric analysis of $10^4$ living cells background staining of the secondary and tertiary antibodies was subtracted and fluorescence values were plotted in the diagram.

Figure 11:
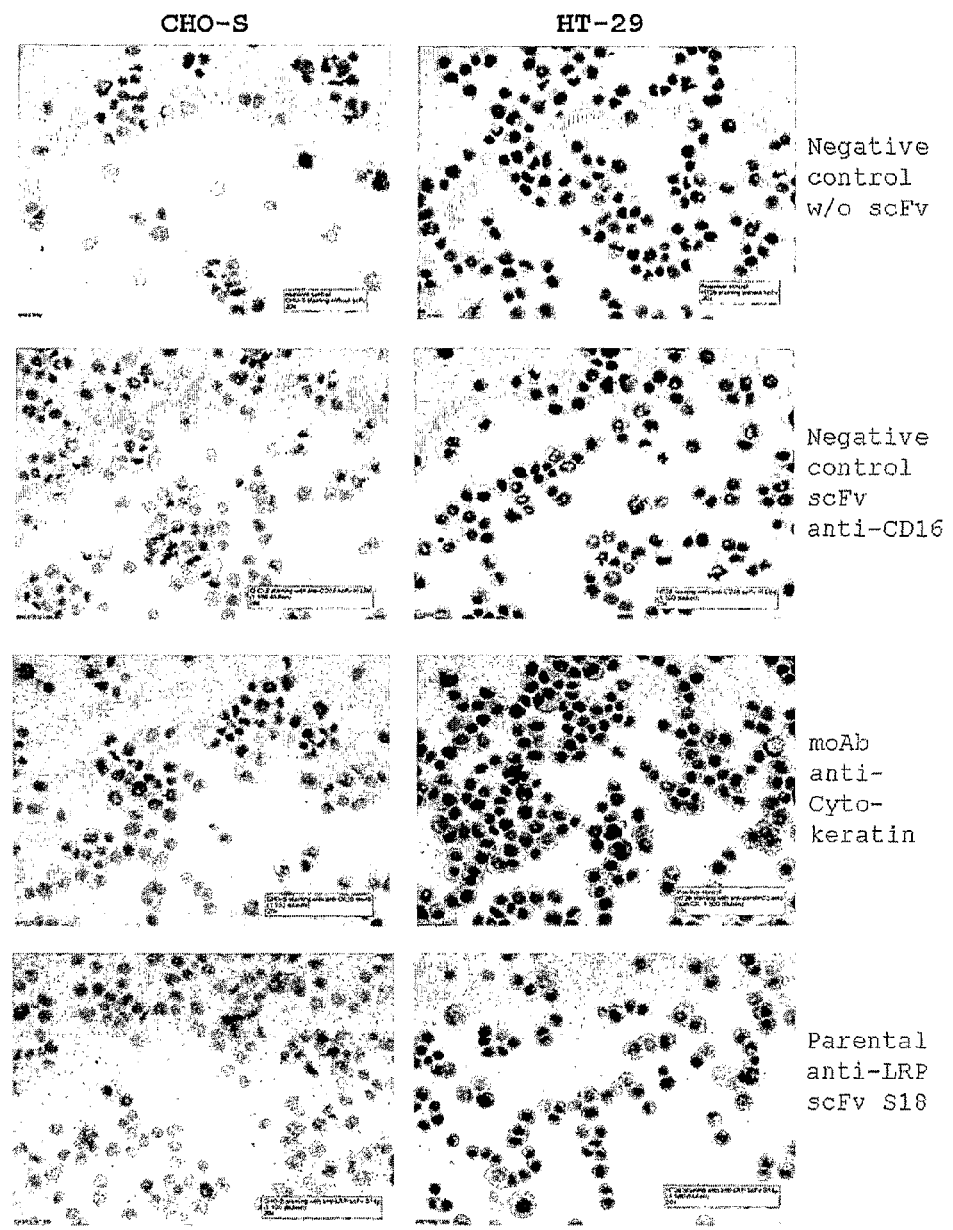

FIG. 11: Staining of fixed CHO-S and HT-29 cells in immune cytology.

$10^5$ CHO-S and HT-29 cells were spun on microscope slides. After PFA fixation the cells were stained by IMAC purified chain shuffled anti-LRP scFvs followed by an anti-His antibody (Novagen) and a monoclonal antibody Multilink Biogenex antibody (Biogenex). The staining reaction was performed with Streptavidin-AP and FastRed (Biogenex). The nuclei of cells were finally stained with Mayers Hamalaun solution for improved contrast. Control staining with the 2nd and 3rd antibodies only, or with an irrelevant anti-CD16 scFv, served as negative controls. As positive control a monoclonal antibody against the epithelial marker Cytokeratin 20 was included.

Figure 12:
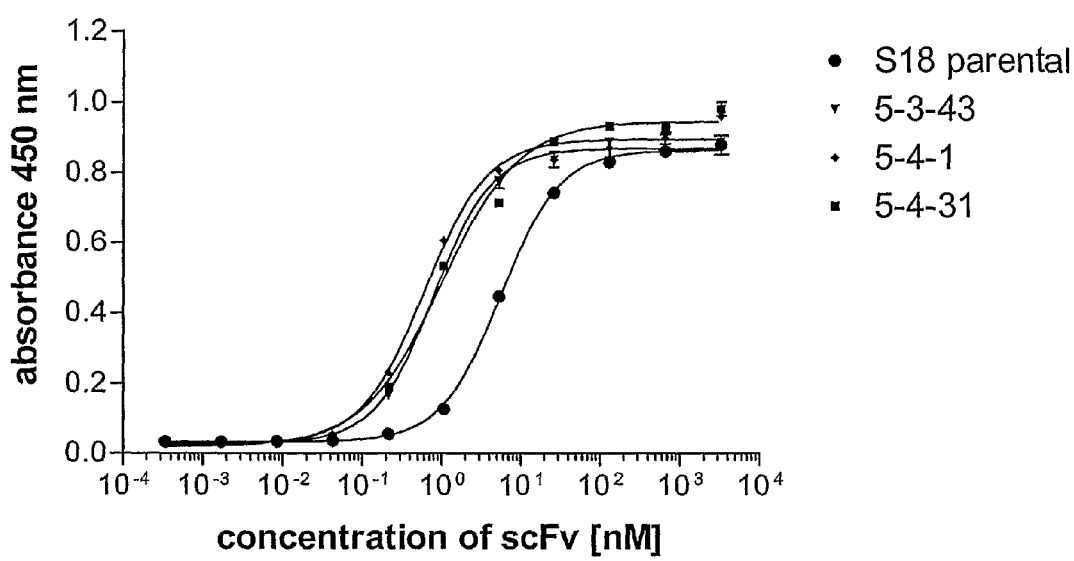

FIG. 12: Titration of chain-shuffled anti-LRP scFv on LRP-GST fusion protein in ELISA.

An ELISA microtiter plate was coated with an LRP-GST fusion protein (200 ng/well) and anti-LRP scFv S18, 5-3-43, 5-4-1- and 5-4-31 were added at the indicated concentrations. Bound scFv were detected with HRP-coupled anti-$(His)_5$ monoclonal antibody. Tetramethylbenzidine was used as a substrate for HRP and enzymatic reaction was stopped with sulphuric acid before measuring the absorbance at 450 nm. The measured absorbance values were plotted in a diagram using GraphPadPrism software for analysis by non-linear regression.

Figure 13:
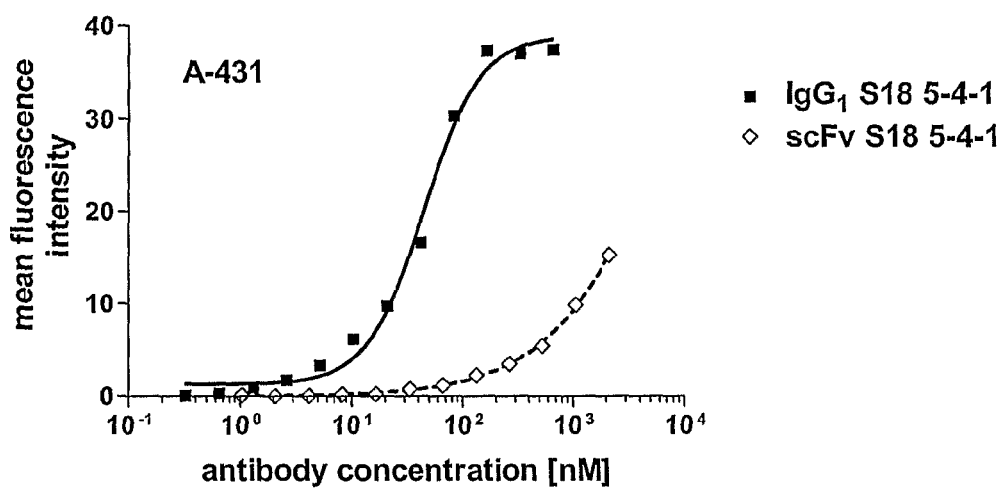
Figure 13:
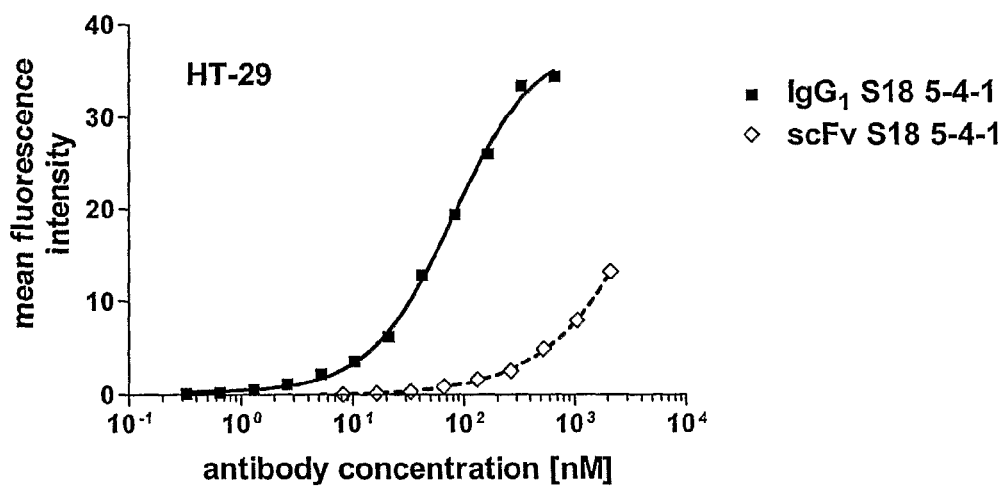

FIG. 13: Binding of scFv S18 5-4-1 and IgG1 S18 5-4-1 to A-431 and HT-29 cells $7 \times 10^5$ A-431 cells (A) or $1 \times 10^6$ HT-29 (B) cells were stained with scFv S18 5-4-1 or IgG1 S18 5-4-1 at the indicated concentrations. Cell surface bound scFv were detected with anti-His mAb 13/45/31-2 (10 μg/mL) followed by FITC-conjugated goat anti-mouse IgG antibodies (15 μg/mL). The human IgG1 was detected by FITC-conjugated goat anti-human IgG antibodies (15 μg/mL). After flow cytometric analysis of $10^4$ living cells background staining of the secondary and tertiary antibodies was subtracted and fluorescence values were used for analysis using the GraphPadPrism software.

Thus, the present invention relates to the use of an antibody, preferably a human antibody, or fragment thereof specifically recognizing an epitope of the laminin receptor or its precursor, a polynucleotide encoding said antibody or fragment thereof or an expression vector containing said polynucleotide for the preparation of a pharmaceutical composition for diagnosing or treating several types of cancer, e.g. B-cell chronic lymphocytic leukemia (B-CLL), non-Hodgkin's lymphoma, Hodgkin's lymphoma, lung cancer, colon carcinoma, mammary carcinoma, pancreatic carcinoma, prostate cancer, metastasising cancers, minimal residual disease.

The antibodies for the use of the present invention can be prepared by methods known to the person skilled in the art, e.g. by the following methods:

(a) Construction of single chain Fv-antibodies by combining the genes encoding at least two immunoglobulin variable $V_H$ and $V_L$ domains, either separated by peptide linkers or by no linkers, into a single genetic construct and expressing it in bacteria or other appropriate expression system.

(b) Non-covalent dimerization or multimerization of single chain Fv-antibodies comprising at least two $V_H$ and $V_L$ specific to the laminin receptor epitope either separated by peptide linkers or by no linkers, in an orientation preventing their intramolecular pairing.

Moreover, the antibodies can be selected according to the screening method described in the examples, below.

The antibody for use in the present invention or the fragment thereof may be a monovalent, bivalent or multivalent antibody.

In a further preferred use, said antibody or fragment thereof is a $F(ab')_2$ fragment, a Fab fragment scFv, a bi-specific scFv, a tri-specific scFv, a single chain or tandem diabody, a single domain antibody (dAb), a minibody or a molecular recognition unit (MRU).

In a more preferred embodiment, the present invention relates to a use, wherein said antibody or fragment thereof comprises a variable $V_H$ region comprising an amino acid sequence as shown in FIG. 6a (N3) or FIG. 6b (S18) and/or a variable $V_L$ region comprising an amino acid sequence as shown in FIG. 6a (N3) or FIG. 6b (S18).

In an even more preferred embodiment, the present invention relates to the use of an antibody or fragment thereof additionally comprising at least one further antigen-interaction site and/or at least one further effector domain. This could be achieved by conversion of the aforementioned antibody fragment into a monospecific full-length immunoglobulin (Ig) G format where the $V_H$ and $V_L$ domains are fused to the constant domains of the heavy and light chain, respectively. Alternatively, a bispecific tetravalent antibody (Tandab) having two additional antigen-interaction sites of another specificity could be generated (Kipriyanov et al. 1999. J. Mol. Biol. 293: 41-56). Preferably, said antigen-interaction site is specific for one or more cell surface molecules with cell surface molecules expressed on human NK cells, T cells, monocytes, macrophages or granulocytes being particularly preferred. Such bispecific molecules (Tandabs) can make a bridge between an LRP-positive tumor cell (e.g. B-CLL cell) and an effector cell of the human immune system (NK cell, T cell, monocyte, macrophage or granulocyte) thus permitting killing of the tumour cell. The efficient killing of various cancer cells expressing the laminin receptor or its precursor may depend on which epitope of the antigen is bound by the antibody. For example, binding alone to the epitope may be sufficient to induce apoptosis through the signalling pathway of the receptor. In this case, monovalent or bivalent antibody fragments are sufficient for the destruction of tumor cells. In another case, crosslinking of the receptor may be necessary for the induction of an apoptotic signal. IgG1 antibodies are found to be appropriate antibodies for both inducing an apoptotic signal by crosslinking the receptor and also by ADCC (antibody dependent cytoxicity). Tumor cells can also be destroyed by recruiting cytotoxic cells of the immune system, such as natural killer cells or cytotoxic T cells. This can be achieved, for example, by generating bispecific antibodies that bind both to the laminin receptor precursor or the mature receptor, respectively, and to a cytotoxic immune cell. The tight binding of the tumor cell and the cytotoxic cell induces the destruction of the tumor cell.

Examples of particularly preferred cell surface molecules are the antigens CD2, CD3, CD16, CD64, CD89; NKp30, NKp44, NKp46, NKp80 (KLR-F1), NKG2C and NKG2D.

The present invention also relates to the use of a polynucleotide encoding an antibody of the present invention or fragment thereof and vectors, preferably expression vectors containing said polynucleotides. The recombinant vectors can be constructed according to methods well known to the person skilled in the art; see, e.g., Sambrook, Molecular Cloning A Laboratory Manual, Cold Spring Harbor Laboratory (1989) N.Y.

A variety of expression vector/host systems may be utilized to contain and express sequences encoding the antibody of the present invention. These include, but are not limited to, microorganisms such as bacteria transformed with recombinant bacteriophage, plasmid, or cosmid DNA expression vectors, yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector-enhancers, promoters, 5' and 3' untranslated regions which interact with host cellular proteins to carry out transcription and translation.

Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript™ phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding the multivalent multimeric antibody, vectors based on SV40 or EBV may be used with an appropriate selectable marker.

In bacterial systems, a number of expression vectors may be selected depending upon the use intended for the antibody of the present invention. Vectors suitable for use in the present invention include, but are not limited to the pSKK expression vector for expression in bacteria.

In yeast (*Saccharomyces cerevisiae*) a number of vectors containing constitutive or inducible promoters such as alpha factor, alcohol oxidase, and PGH may be used; for reviews, see Grant et al. (1987) Methods Enzymol. 153:516-544.

In cases where plant expression vectors are used, the expression of sequences encoding the antibody of the present invention may be driven by any of a number of promoters. For example, viral promoters such as the 35S and 19S promoters of CaMV may be used alone or in combination with the omega leader sequence from TMV (Takamatsu, N. (1987) EMBO J. 6:307-311). Alternatively, plant promoters such as the small subunit of RUBISCO or heat shock promoters may be used (Coruzzi, G. et al. (1984) EMBO J. 3:1671-1680; Broglie, R. et al. (1984) Science 224:838-843; and Winter, J. et al. (1991) Results Probl. Cell Differ. 17:85-105). These constructs can be introduced into plant cells by direct DNA transformation or pathogen-mediated transfection. Such techniques are described in a number of generally available reviews (see, for example, Hobbs, S, and Murry, L. E. in McGraw Hill Yearbook of Science and Technology (1992) McGraw Hill, New York, N.Y.; pp. 191-196.

An insect system may also be used to express the antibodies of the present invention. For example, in one such system, *Autographa californica* nuclear polyhedrosis virus (AcNPV) is used as a vector to express foreign genes in *Spodoptera frugiperda* cells or in *Trichoplusia* larvae. The sequences encoding said antibodies may be cloned into a non-essential region of the virus, such as the polyhedrin gene, and placed under control of the polyhedrin promoter. Successful insertion of the gene encoding said antibody will render the polyhedrin gene inactive and produce recombinant virus lacking coat protein. The recombinant viruses may then be used to infect, for example, *S. frugiperda* cells or *Trichoplusia* larvae in which APOP may be expressed (Engelhard, E. K. et al. (1994) Proc. Nat. Acad. Sci. 91:3224-3227).

In mammalian host cells, a number of viral-based expression systems may be utilised. In cases where an adenovirus is used as an expression vector, sequences encoding an antibody of the present invention may be ligated into an adenovirus transcription/translation complex consisting of the late promoter and tripartite leader sequence. Insertion in a non-essential E1 or E3 region of the viral genome may be used to obtain a viable virus which is capable of expressing the antibody in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10 M are constructed and delivered via conventional delivery methods (liposomes, polycationic amino polymers, or vesicles) for therapeutic purposes.

Specific initiation signals may also be used to achieve more efficient translation of sequences encoding the antibody of the present invention. Such signals include the ATG initiation codon and adjacent sequences. In cases where sequences encoding the antibody, its initiation codon, and upstream sequences are inserted into the appropriate expression vector, no additional transcriptional or translational control signals may be needed. However, in case where only coding sequence is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf et al. (1994) Results Probl. Cell Differ. 20:125-162).

In addition, a host cell strain may be chosen for its ability to modulate the expression of the inserted sequences or to process the expressed antibody chains in the desired fashion. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; Bethesda, Md.) and may be chosen to ensure the correct modification and processing of the foreign antibody chains.

For long-term, high-yield production of recombinant antibodies, stable expression is preferred. For example, cell lines which stably express the antibody may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al. (1977) Cell 11:223-32) and adenine phosphoribosyltransferase (Lowy et al. (1980) Cell 22:817-23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler et al. (1980) Proc. Natl. Acad. Sci. 77:3567-70); npt, which confers resistance to the aminoglycosides neomycin and G-418 (Colbere-Garapin et al. (1981) J. Mol. Biol. 150:1-14) and als or pat, which confer resistance to chlorsulfuron and phosphinotricin acetyltransferase, respectively. Additional selectable genes have been described, for example, trpB, which allows cells to utilize indole in place of tryptophan, or hisD, which allows cells to utilize histinol in place of histidine (Hartman and Mulligan (1988) Proc. Natl. Acad. Sci. 85:8047-51). Recently, the use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes et al. (1995) Methods Mol. Biol. 55:121-131).

A particular preferred expression vector for expression in *E. coli* is pSKK2 (LeGall et al., J Immunol Methods. (2004) 285(1):111-27).

For use in preventing or treating the various mentioned cancer types, in particular B-CLL, preferably by immunotherapy or gene therapy, the composition containing an antibody, polynucleotide or an expression vector as described above is preferably combined with a suitable pharmaceutical carrier. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Administration of the suitable compositions may be effected by different ways, e.g. by intravenous, intraperetoneal, subcutaneous, intramuscular, topical or intradermal administration. The route of administration, of course, depends on the kind of therapy and the kind of compound contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind of therapy, general health and other drugs being administered concurrently.

Finally, the present invention also relates to the use of an antibody or fragment thereof as described above for the preparation of a diagnostic composition for the diagnosis of various cancer types, e.g. B-cell chronic lymphocytic leukemia (B-CLL), non-Hodgkin's lymphoma, Hodgkin's lymphoma, lung cancer, colon carcinoma, mammary carcinoma, pancreatic carcinoma, prostate cancer, metastasising cancers, minimal residual disease. For such an assay the antibody or fragment thereof, can be detectably labelled, for example, with a radioisotope, a bioluminescent compound, a chemiluminescent compound, a fluorescent compound, a metal chelate, or an enzyme (e.g. horse-radish peroxidase, alkaline phosphatase, β-galactosidase, malate dehydrogenase, glucose oxidase, urease, catalase etc.) which, in turn, when later exposed to a substrate will react to the substrate in such a manner as to produce a chemical moiety which can be detected. The antibody or fragment thereof can also be immobilized on an insoluble carrier, e.g. glass, polystyrene, polypropylene, polyethylene, dextran, nylon, natural and modified celluloses, polyacrylamides, agarose and magnetic beads.

Examples of immunoassays suitable for the diagnostic use of the present invention are competitive or sandwich assays, such as the enzyme linked immunosorbent assay (ELISA), the radioimmunoassay (RIA) or Western Blots. Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99}$mTc), and fluorescent labels, such as fluorescein and rhodamine.

The below examples explain the invention in more detail.

EXAMPLE 1

Library Construction (A) Construction of a Human Combinatorial IgM Antibody Library A large human IgM-derived scFv phage display library was generated as previously described (Dörsam et al., FEBS Lett. 414 (1997), 7-13; Little et al., J. Immunol. Methods 231 (1999), 3-9; Schwarz et al., FASEB J. 18(14) (2004), 1704-6. Epub 2004 Sep. 16). The mRNA was isolated from peripheral blood lymphocytes (PBL) of five healthy human donors and from spleen biopsy material of six additional donors and was transcribed into cDNA. The cDNA of each donor was used separate as a template in a two-step PCR amplification process. The genes encoding the antibody variable domains ($V_H$ and $V_L$) were first amplified using primers specific for μ, λ and κ chains.

| Heavy chain primer 1$^{st}$ PCR | | |
|---|---|---|
| Forward primer: | | |
| VH-1a. | CAG GTG CAG CTG GTG CAG TCT | (SEQ ID NO: 8) |
| VH-1b. | CAG GTC CAG CTT GTG CAG TCT | (SEQ ID NO: 9) |
| VH-1c. | CAG GTC CAG CTG GTA CAG TCT | (SEQ ID NO: 10) |
| VH-1d. | GAG GTC CAG CTG GTA CAG TCT | (SEQ ID NO: 11) |
| VH-1e. | CAG ATG CAG CTG GTA CAG TCT | (SEQ ID NO: 12) |
| VH-2a. | CAG ATC ACC TTG AAG GAG TCT | (SEQ ID NO: 13) |
| VH-2b. | CAG GTC ACC TTG AAG GAG TCT | (SEQ ID NO: 14) |
| VH-3a. | GAA GTG CAG CTG GTG GAG TCT | (SEQ ID NO: 15) |
| VH-3b. | CAG GTG CAG CTG GTG GAG TCT | (SEQ ID NO: 16) |
| VH-3c. | GAG GTG CAG CTG TTG GAG TCT | (SEQ ID NO: 17) |
| VH-4a. | CAG GTG CAG CTG CAG GAG TCG | (SEQ ID NO: 18) |
| VH-4b. | CAG CTG CAG CTG CAG GAG TCG | (SEQ ID NO: 19) |
| VH-4c. | CAG GTG CAG CTA CAG CAG TGG | (SEQ ID NO: 20) |

| | | |
|---|---|---|
| VH-5 | GAA GTG CAG CTG GTG CAG TCT | (SEQ ID NO: 21) |
| VH-6 | CAG GTA CAG CTG CAG CAG TCA | (SEQ ID NO: 22) |
| VH-7 | CAG GTG CAG CTG GTG CAA TCT | (SEQ ID NO: 23) |

Backward primer:

| | | |
|---|---|---|
| IgM | AAG GGT TGG GGC GGA TGC ACT | (SEQ ID NO: 24) |

Lambda light chain primer 1st PCR

Forward primer, lambda:

| | | |
|---|---|---|
| Vλ-1a. | CAG TCT GTG CTG ACG CAG CCA | (SEQ ID NO: 25) |
| Vλ-1b. | CAG TCT GTG CTG ACG CAG CCG | (SEQ ID NO: 26) |
| Vλ-2 | CAG TCT GCC CTG ACT CAG CCT | (SEQ ID NO: 27) |
| Vλ-3a. | TCC TAT GAG CTG ACA CAG CCA | (SEQ ID NO: 28) |
| Vλ-3b. | TCC TCT GAG CTG ACA CAG GAC | (SEQ ID NO: 29) |
| Vλ-3c. | TCC TAT GTG CTG ACA CAG CCA | (SEQ ID NO: 30) |
| Vλ-3d. | TCC TAT GAG CTG ACA CAG CTA | (SEQ ID NO: 31) |
| Vλ-3e. | TCC TAT GAG CTG ATG CAG CCA | (SEQ ID NO: 32) |
| Vλ-4a. | CTG CCT GTG CTG ACT CAG CCC | (SEQ ID NO: 33) |
| Vλ-4b. | CAG CCT GTG CTG ACT CAA TCA | (SEQ ID NO: 34) |
| Vλ-4c. | CAG CTT GTG CTG ACT CAA TCG | (SEQ ID NO: 35) |
| Vλ-5a. | CAG CCT GTG CTG ACT CAG CCA | (SEQ ID NO: 36) |
| Vλ-5b. | CAG GCT GTG CTG ACT CAG CCG | (SEQ ID NO: 37) |
| Vλ-6 | AAT TTT ATG CTG ACT CAG CCC | (SEQ ID NO: 38) |
| Vλ-7a. | CAG ACT GTG GTG ACT CAG GAG | (SEQ ID NO: 39) |
| Vλ-7b. | CAG GCT GTG GTG ACT CAG GAG | (SEQ ID NO: 40) |
| Vλ-8 | CAG ACT GTG GTG ACC CAG GAG | (SEQ ID NO: 41) |
| Vλ-9 | CAG CCT GTG CTG ACT CAG CCA | (SEQ ID NO: 42) |
| Vλ-10 | CAG GCA GGG CTG ACT CAG CCA | (SEQ ID NO: 43) |

Backward primer, lambda:

| | | |
|---|---|---|
| C-λ | GGA OGG CGG GAA CAG AGT GAC | (SEQ ID NO: 44) |

Kappa light chain primer 1st PCR

Forward primer, kappa:

| | | |
|---|---|---|
| Vκ-1a. | GAC ATC CAG ATG ACC CAG TCT | (SEQ ID NO: 45) |
| Vκ-1b. | AAC ATC CAG ATG ACC CAG TCT | (SEQ ID NO: 46) |
| Vκ-1c. | GCC ATC CAG TTG ACC CAG TCT | (SEQ ID NO: 47) |
| Vκ-1d. | GAC ATC CAG TTG ACC CAG TCT | (SEQ ID NO: 48) |
| Vκ-1e. | GCC ATC CGG ATG ACC CAG TCT | (SEQ ID NO: 49) |
| Vκ-1f. | GTC ATC TGG ATG ACC CAG TCT | (SEQ ID NO: 50) |
| Vκ-1g. | GCC ATC CAG ATG ACC CAG TCT | (SEQ ID NO: 51) |
| Vκ-2a. | GAT ATT GTG ATG ACC CAG ACT | (SEQ ID NO: 52) |
| Vκ-2b. | GAT GTT GTG ATG ACT CAG TCT | (SEQ ID NO: 53) |
| Vκ-2c. | GAT ATT GTG ATG ACT CAG TCT | (SEQ ID NO: 54) |
| Vκ-3a. | GAA ATT GTG TTG ACG CAG TCT | (SEQ ID NO: 55) |
| Vκ-3b. | GAA ATT GTG ATG ACG CAG TCT | (SEQ ID NO: 56) |
| Vκ-3c. | GAA ATT GTA ATG ACG CAG TCT | (SEQ ID NO: 57) |
| Vκ-4 | GAC ATC GTG ATG ACC CAG TCT | (SEQ ID NO: 58) |
| Vκ-5 | GAA ACG ACA CTC ACG CAG TCT | (SEQ ID NO: 59) |
| Vκ-6a. | GAA ATT GTG CTG ACT CAG TCT | (SEQ ID NO: 60) |
| Vκ-6b. | GAT GTT GTG ATG ACA CAG TCT | (SEQ ID NO: 61) |

Backward primer, kappa:

| | | |
|---|---|---|
| C-κ | GAC AGA TGG TGC AGO CAC AGT | (SEQ ID NO: 62) |

The obtained fragments were reamplified with a homologous set of primer., which introduced the restriction sites for cloning purposes (NcoI and HindIII for $V_H$ and MluI and NotI for $V_L$) (Little et al., 1999).

| heavy chain primer, 2$^{nd}$ PCR | | |
|---|---|---|
| Forward primer: | | |
| | *Nco*I | |
| VH-1a. | TGG ACG CCC ATG GCG CAG GTG CAG CTG GTG CAG TCT | (SEQ ID NO: 63) |
| VH-1b. | TGG ACG CCC ATG GCG CAG GTC CAG CTT GTG CAG TCT | (SEQ ID NO: 64) |
| VH-1c. | TGG ACG CCC ATG GCG CAG GTC CAG CTG GTA CAG TCT | (SEQ ID NO: 65) |
| VH-1d. | TGG ACG CCC ATG GCG GAG GTC CAG CTG GTA CAG TCT | (SEQ ID NO: 66) |
| VH-1e. | TGG ACG CCC ATG GCG CAG ATG CAG CTG GTA CAG TCT | (SEQ ID NO: 67) |
| VH-2a. | TGG ACG CCC ATG GCG CAG ATC ACC TTG AAG GAG TCT | (SEQ ID NO: 68) |
| VH-2b. | TGG ACG CCC ATG GCG CAG GTC ACC TTG AAG GAG TCT | (SEQ ID NO: 69) |
| VH-3a. | TGG ACG CCC ATG GCG GAA GTG CAG CTG GTG GAG TCT | (SEQ ID NO: 70) |
| VH-3b. | TGG ACG CCC ATG GCG CAG GTG CAG CTG GTG GAG TCT | (SEQ ID NO: 71) |
| VH-3c. | TGG ACG CCC ATG GCG GAG GTG CAG CTG TTG GAG TCT | (SEQ ID NO: 72) |
| VH-4a. | TGG ACG CCC ATG GCG CAG GTG CAG CTG CAG GAG TCG | (SEQ ID NO: 73) |
| VH-4b. | TGG ACG CCC ATG GCG CAG CTG CAG CTG CAG GAG TCG | (SEQ ID NO: 74) |
| VH-4c. | TGG ACG CCC ATG GCG CAG GTG CAG CTA CAG GAG TGG | (SEQ ID NO: 75) |
| VH-5 | TGG ACG CCC ATG GCG GAA GTG CAG CTG GTG CAG TCT | (SEQ ID NO: 76) |
| VH-6 | TGG ACG CCC ATG GCG CAG GTA CAG CTG CAG CAG TCA | (SEQ ID NO: 77) |
| VH-7 | TGG ACG CCC ATG GCG CAG GTG CAG CTG GTG CAA TCT | (SEQ ID NO: 78) |
| Backward primer: | | |
| | *Hind*III | |
| IgM | TGG GAA AAG CTT AAG GGT TGG GGC GGA TGC ACT | (SEQ ID NO: 79) |
| Lambda light chain primer, 2$^{nd}$ PCR | | |
| Forward primer, lambda: | | |
| | *Mlu*I | |
| Vλ-1a. | CCT ACA GAA CGC GTA CAG TCT GTG CTG ACG CAG CCA | (SEQ ID NO: 80) |
| Vλ-1b. | CCT ACA GAA CGC GTA CAG TCT GTG CTG ACG CAG CCG | (SEQ ID NO: 81) |
| Vλ-2 | CCT ACA GAA CGC GTA CAG TCT GCC CTG ACT CAG CCT | (SEQ ID NO: 82) |
| Vλ-3a. | CCT ACA GAA CGC GTA TCC TAT GAG CTG ACA CAG CCA | (SEQ ID NO: 83) |
| Vλ-3b. | CCT ACA GAA CGC GTA TCC TGT GAG CTG ACA CAG GAC | (SEQ ID NO: 84) |
| Vλ-3c. | CCT ACA GAA CGC GTA TCC TAT GTG CTG ACA CAG CCA | (SEQ ID NO: 85) |
| Vλ-3d. | CCT ACA GAA CGC GTA TCC TAT GAG CTG ACA CAG CTA | (SEQ ID NO: 86) |
| Vλ-3e. | CCT ACA GAA CGC GTA TCC TAT GAG CTG ATG CAG CCA | (SEQ ID NO: 87) |
| Vλ-4a. | CCT ACA GAA CGC GTA CTG CCT GTG CTG ACT CAG CCC | (SEQ ID NO: 88) |
| Vλ-4b. | CCT ACA GAA CGC GTA CAG CCT GTG CTG ACT CAA TCA | (SEQ ID NO: 89) |
| Vλ-4c. | CCT ACA GAA CGC GTA CAG CTT GTG CTG ACT CAA TCG | (SEQ ID NO: 90) |
| Vλ-5a. | CCT ACA GAA CGC GTA CAG CCT GTG CTG ACT CAG CCA | (SEQ ID NO: 91) |
| Vλ-5b. | CCT ACA GAA CGC GTA CAG GGT GTG CTG ACT CAG CCG | (SEQ ID NO: 92) |
| Vλ-6 | CCT ACA GAA CGC GTA AAT TTT ATG CTG ACT CAG CCC | (SEQ ID NO: 93) |
| Vλ-7a. | CCT ACA GAA CGC GTA CAG ACT GTG GTG ACT CAG GAG | (SEQ ID NO: 94) |
| Vλ-7b. | CCT ACA GAA CGC GTA CAG GCT GTG GTG ACT CAG GAG | (SEQ ID NO: 95) |
| Vλ-8 | CCT ACA GAA CGC GTA CAG ACT GTG GTG ACC CAG GAG | (SEQ ID NO: 96) |

```
Vλ-9    CCT ACA GAA CGC GTA CAG CCT GTG CTG ACT CAG CCA       (SEQ ID NO: 97)

Vλ-10   CCT ACA GAA CGC GTA CAG GCA GGG CTG ACT CAG CCA       (SEQ ID NO: 98)
```

Backward primer, lambda:

```
                        NotI
C-λ     GGG CGG CAG GGC GGC CGC GGA CGG CGG GAA CAG AGT GAC   (SEQ ID NO: 99)
```

Kappa light chain primer, 2nd PCR

Forward primer, kappa:

```
                    MluI
Vκ-1a.  CCT ACA GAA CGC GTA GAC ATC CAG ATG ACC CAG TCT       (SEQ ID NO: 100)

Vκ-1b.  CCT ACA GAA CGC GTA AAC ATC CAG ATG ACC CAG TCT       (SEQ ID NO: 101)

Vκ-1c.  CCT ACA GAA CGC GTA GCC ATC CAG TTG ACC CAG TCT       (SEQ ID NO: 102)

Vκ-1d.  CCT ACA GAA CGC GTA GAC ATC CAG TTG ACC CAG TCT       (SEQ ID NO: 103)

Vκ-1e.  COT ACA GAA CGC GTA GCC ATC CGG ATG ACC CAG TCT       (SEQ ID NO: 104)

Vκ-1f.  CCT ACA GAA CGC GTA GTC ATC TGG ATG ACC CAG TCT       (SEQ ID NO: 105)

Vκ-1g.  CCT ACA GAA CGC GTA GCC ATC CAG ATG ACC CAG TCT       (SEQ ID NO: 106)

Vκ-2a.  CCT ACA GAA CGC GTA GAT ATT GTG ATG ACC CAG ACT       (SEQ ID NO: 107)

Vκ-2b.  CCT ACA GAA CGC GTA GAT GTT GTG ATG ACT CAG TCT       (SEQ ID NO: 108)

Vκ-2c.  CCT ACA GAA CGC GTA GAT ATT GTG ATG ACT CAG TCT       (SEQ ID NO: 109)

Vκ-3a.  CCT ACA GAA CGC GTA GAA ATT GTG TTG ACG CAG TOT       (SEQ ID NO: 110)

Vκ-3b.  CCT ACA GAA CGC GTA GAA ATT GTG ATG ACG CAG TCT       (SEQ ID NO: 111)

Vκ-3c.  CCT ACA GAA CGC GTA GAA ATT GTA ATG ACG CAG TCT       (SEQ ID NO: 112)

Vκ-4    CCT ACA GAA CGC GTA GAC ATC GTG ATG ACC CAG TCT       (SEQ ID NO: 113)

Vκ-5    CCT ACA GAA CGC GTA GAA ACG ACA CTC ACG CAG TCT       (SEQ ID NO: 114)

Vκ-6a.  COT ACA GAA CGC GTA GAA ATT GTG CTG ACT CAG TCT       (SEQ ID NO: 115)

Vκ-6b.  CCT ACA GAA CGC GTA GAT GTT GTG ATG ACA CAG TOT       (SEQ ID NO: 116)
```

Backward primer, kappa:

```
                       NotI
C-κ     GGG CGG CAG GGC GGC CGC GAC AGA TGG TGC AGC CAC AGT   (SEQ ID NO: 117)
```

For phage surface display, the phagemid pEXHAM1 was generated from pSEX81 (Welschof et al., Proc. Natl. Acad. Sci. USA 94 (1995), 1902-7) by inserting the DNA sequences of six histidines ($His_6$ tag), an amber stop codon, and of a c-myc-epitope between the scFv coding sequence and the pIII gene of M13 phage. The genes encoding the antibody $V_H$ domains were ligated into pEXHAM1 vector and the derived DNA was used for transformation of E. coli XL1-blue cells, thus resulting in five PBL-derived and six spleen-derived sub-libraries, ranging in size between $1.5 \times 10^6$ and $7.7 \times 10^7$ individual clones. The genes of lambda and kappa chain variable domains from each donor were ligated separately into the corresponding $V_H$ sub-library by a series of transformations yielding in a total complexity of $1.8 \times 10^9$ single clones ($7.9 \times 10^8$ clones PBL-derived and $9.6 \times 10^8$ spleen-derived).

(B) Construction of the Synthetic $V_H$ Library

A synthetic scFv library with mutated $V_H$ chains was generated using two scFvs originally isolated from a large human scFv library as master frameworks. The selected master frameworks E4 and 09 are specific for estradiol and for surface antigen of hepatitis B virus, respectively (Dörsam et al., 1997; Schwarz et al., 2004). The coding sequences of the $V_H$ CDR3s of both master frameworks were replaced by synthetic oligodeoxynucleotides that contained the sequence TGT GCG ARA $(NNK)_{4-7}$ TTT GAS (with S=G or C) TAC encoding CDR3 loops of 7 to 10 amino acids of the partly randomized amino acid sequence C A K/R X4-7 F E/D Y. Oligos were cloned separately into pEXHAM1 derivatives containing E4 or 09 scFv-genes, thus resulting in two libraries of $3.2 \times 10^8$ (E4) and $2.9 \cdot 10^8$ (C9) independent clones after transformation of E. coli XL1-blue.

Four subgroups of transformants containing 4, 5, 6 or 7 randomized amino acids were generated. Each subgroup contains a number of independent clones exceeding the calculated combinatorial diversity. In the case of 7 permutations a diversity of $10^8$ was generated. Additionally, the CDR-H3 of 09 and E4 were replaced by CDR3 coding sequences amplified by PCR from PBL- and spleen-derived cDNA of human donors prior used for the construction of the natural library.

Transformation of E. coli XL1-blue resulted in further 10⁸ individual clones. In total, the complexity of the generated synthetic antibody library was 7.1×10⁸ independent clones.

EXAMPLE 2

Selection on Recombinant LRP-GST Fusion Protein

Three rounds of selection were performed on a LRP-GST fusion protein expressed in Baculovirus infected Sf9 cells, which was kindly provided by Dr. Weiss (University Munich) (Rieger et al., Nat. Med. 3 (1997), 1383-8), keeping the naïve and the synthetic library separately. Approximately $10^{12}$ phages from each library resuspended in PBS, 0.1% tween, 2% skim milk were incubated with polystyrene immobilized LRP-GST. Phages that did not specifically bind to the target antigen were removed by ten washing steps with PBS, 0.1% tween. Bound entities were eluted by using Glycine-HCl, pH 2.2, and after neutralisation with 2 M Tris/HCl, pH 8, the eluate was used for infection of freshly grown E. coli XL1 Blue cells (mid log. Phase $OD_{600}$ 0.2-0.5). Cells successfully transduced with phagemids encoding the human scFvs were selected for ampicillin resistance and were subsequently infected with M13K07 helper phage to generate phage progeny displaying scFv for the following in vitro selection. After the 3$^{rd}$ round of selection individual colonies were grown in LB medium containing 100 µg/mL ampicillin and 20 µg/mL tetracycline at 30° C. in a PP-Masterblock 2 mL (Greiner, Frickenhausen, Germany). Cells were harvested by centrifugation and resuspended in 200 µL 200 mM Tris-HCl, pH 7.5, 20% Sucrose, 1 mM EDTA. During incubation for one hour on ice the outer membrane is destroyed so that soluble periplasmic proteins including the scFv are released into the liquid. After elimination of spheroplasts and cellular debris by centrifugation, the crude periplasmic extracts were tested in ELISA for scFv antibody fragments binding the LRP-GST fusion protein.

Figure 1A:
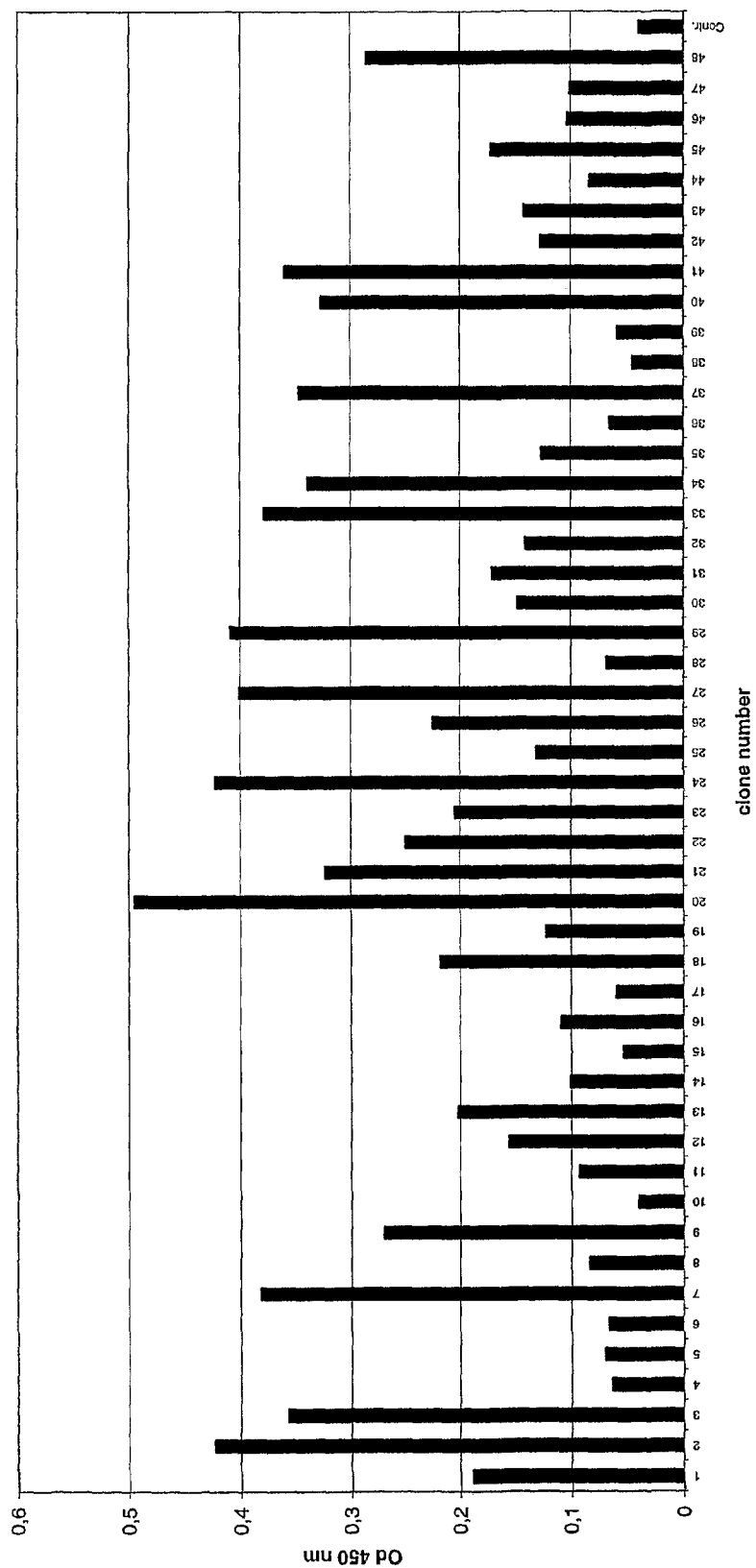
FIGS. 1a and 1b: Analysis of library-derived individual scFv clones for binding to recombinant human LRP-GST fusion protein in ELISA.
 (a) Analysis of scFvs isolated from the naïve library.
 (b) Analysis of scFvs isolated from the synthetic library.
 200 ng LRP-GST was coated per each well overnight in 0.1 M NaHCO$_3$, pH 8.6, and blocked with PBS, 0.2% skim milk.
Figure 1B:
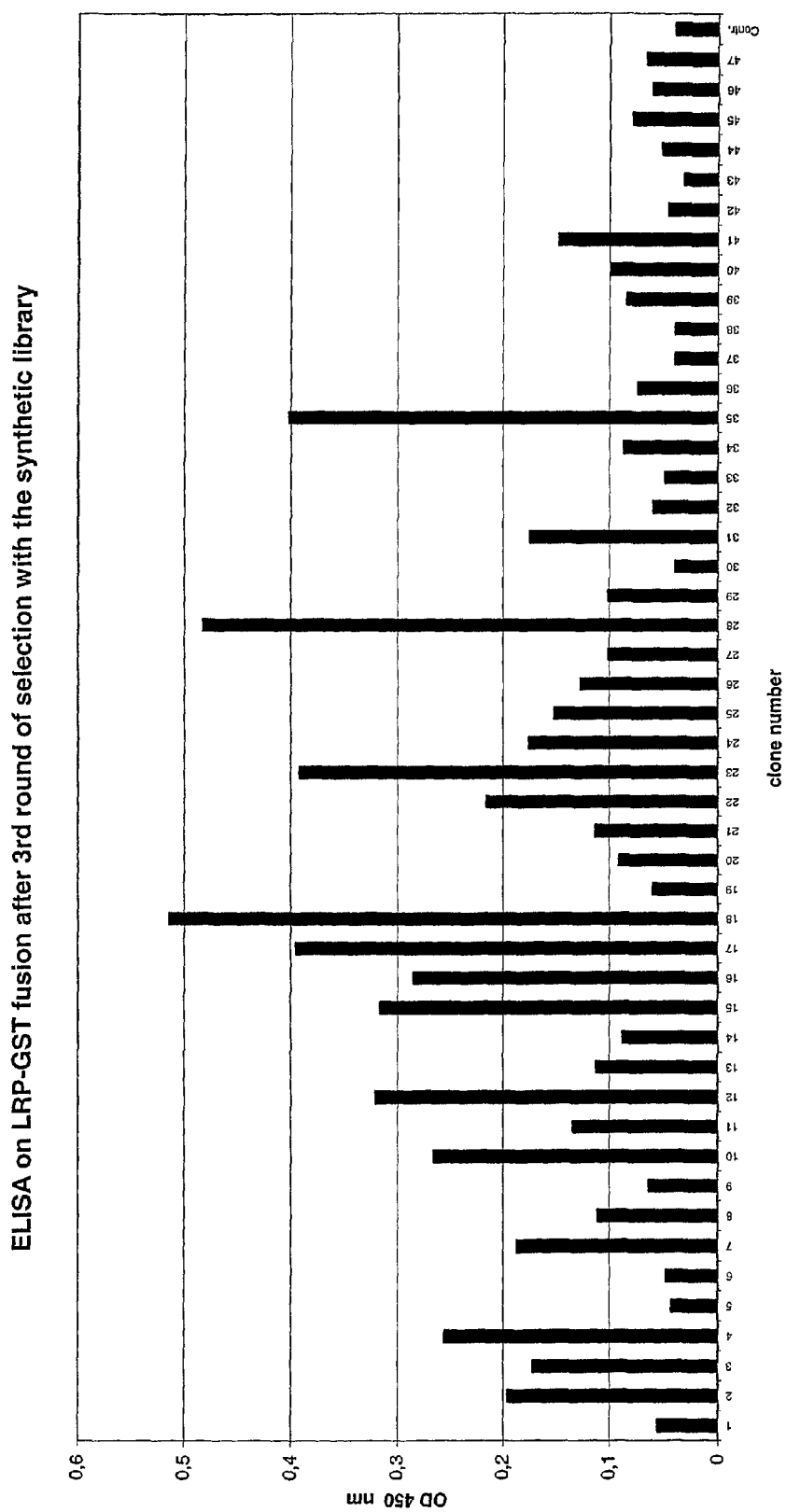

Detection of scFv bound to immobilized LRP-GST (200 ng/well) was carried out by using an anti-Penta His HRP-conjugate (Qiagen, 1 µg/mL). The signal was developed with the tetramethyl benzidine solution (TMB) (KPL) and detected at 450 nm after stopping the reaction with 0.5 M $H_2SO_4$ (FIG. 1a, 1b). 32 out of 48 analyzed clones (66%) derived from the naïve library and 25 out of 47 analyzed clones (53%) from the synthetic library showed positive signals in ELISA on immobilized LRP-GST while demonstrating no binding to GST alone. DNA analysis by restriction digest with BstNI and sequencing demonstrated that 10 out of 13 positive in ELISA natural clones were identical (N3). Another clone (N2) was present twice and the clone N37 revealed an individual restriction pattern. The CDR-H3 sequences of the scFv variants isolated from the synthetic library revealed two different consensus sequences.

EXAMPLE 3

Western Blot Analyses

The scFv variants which were tested positive in ELISA were tested by Western Blot analysis using the recombinant LRP-GST fusion protein and GST alone as a negative control. For this purpose, the crude periplasmic extracts containing selected scFvs were isolated from 5 mL bacterial cultures. The freshly inoculated bacteria were grown overnight at 37° C. in LB medium containing 50 mM glucose, 100 µg/mL ampicillin and 20 µg/mL tetracycline. The overnight cultures were diluted till $OD_{600nm}=0.1$ in LB medium with ampicillin and tetracycline and further grown at 37° C. till $OD_{600nm}=0.8$. The bacteria were harvested by centrifugation and resuspended in LB medium containing 0.1 mM isopropyl-β-D-thiogalactopyranosid (IPTG), 100 µg/mL ampicillin and 20 µg/mL tetracycline. After overnight incubation of induced bacteria at 21° C., 300 µL periplasmic extracts were isolated as described for ELISA. Before using for Western Blot analysis, the periplasmic extracts were dialyzed against PBS.

A mixture of 1 µg LRP-GST and GST was loaded on each lane and the corresponding bands were separated by 12% SDS-PAGE. The protein bands were transferred on a nitrocellulose membrane by electroblotting. After staining with Ponceau S, the membrane was cut into strips of 5 mm width. Each nitrocellulose strip was individually incubated with scFv containing crude periplasmic extracts diluted 1:5 in PBS, 0.1% tween, 2% skim milk. Detection was carried out with the anti-Penta His HRP-conjugate (Qiagen, Hilden, Germany; 1 µg/mL) using diaminobenzidine (DAB) as a peroxidase substrate. Control strips were incubated with diluted polyclonal anti-human LRP rabbit serum W3 (1.3 µg/mL) kindly provided by Dr. Weiss (University Munich) (Rieger et al., 1997) followed by detection with goat anti-rabbit IgG HRP-conjugate (0.2 µg/mL)(Dianova).

The polyclonal anti-human LRP rabbit serum W3 clearly recognized both the LRP-GST fusion protein and the GST protein alone, since the animals were immunized with the fusion protein (FIG. 2). The scFvs N3 (=N40) and N41 derived from the naïve library as well as the synthetic clones S18 and S23 revealed strong signals on the recombinant protein whereas the scFvs N37, S15, S16, S17 reacted significantly weaker either due to a low affinity for the antigen or due to the lower concentration of corresponding scFv in the periplasmic extract. The scFv variant S7 did not interact with the antigen at all. None of the tested scFvs showed cross-reactivity with GST alone. Unlike W3 serum, the LRP-GST fusion protein was detected by scFvs as a double band. This might reflect the presence of the LRP-GST degradation product recognized only by scFvs thus indicating the absence of this specificity in the polyclonal W3 serum.

For further characterization, the highly enriched clone N3 and the clone S18 were selected. The scFvs were subcloned into the expression vector pSKK2 (LeGall et al., J. Immunol. Methods. (2004) 285(1):111-27), transformed into E. coli RV308, expressed in 2 liter shake flask cultures and purified by immobilized metal ion affinity chromatography (IMAC) according to Le Gall et al., (2004) J. Immunol. Methods 285(1), 111-27. Besides the coexpression of the bacterial chaperone Skp/OmpH, recloning the scFv coding sequence into pSKK2 offers an advantage of adding a c-myc tag to its C-terminus for detection purposes. The isolated scFvs were analyzed for their ability to recognize endogenous LRP present in lysates from mammalian cells. Cell lysates were prepared by resuspending 2.5×10⁶ N2a cells in 300 µL lysis-buffer (10 mM Tris-HCl, pH 7.5, 100 mM NaCl, 10 mM EDTA, 0.5% Triton, 0.5% Na-deoxycholat, supplemented with the Complete EDTA-free protease inhibitor cocktail (Roche, Mannheim, Germany). 7.5 µl of this lysate was separated by SDS-PAGE and blotted as described before. Nitrocellulose strips were incubated in buffers containing 3 different salt concentrations (PBS containing 140 mM, 200 mM or 300 mM NaCl, 0.1% Tween, 2% skim milk) with the individual scFvs (1.4 µg/mL) followed by washing steps at respective NaCl concentrations. Detection was carried out by the mouse anti-c-myc mAb 9E10 (0.5 µg/mL), a kind gift from Dr. Moldenhauer (DKFZ), followed by the HRP-conjugated goat anti mouse IgG antibodies (0.5 µg/mL, Dianova). As a positive control, the polyclonal rabbit serum W3 (1.3 µg/mL) was used under the same salt conditions (FIG. 3).

Under all tested NaCl concentrations, both library-derived scFvs and the polyclonal serum W3 recognized the 37 kDa precursor. At NaCl concentration of 140 mM, all three scFvs revealed slight background binding which could be diminished by increasing the salt concentration. The protein band corresponding to approximately 67 kDa remained constantly visible in case of detection with the scFv N3, thus reflecting potential binding to the 67 kDa mature LR. This finding indicates that N3 presumably binds to both LR and LRP, whereas scFv S18 might be specific for the 37 kDa LRP.

EXAMPLE 4

Analyses of Binding by Flow Cytometry (FACS)

The IMAC purified scFvs N3 and S18 were tested for their ability to bind to the native protein on the surface of murine and human tumor cell lines. Since the 37LRP/p40 protein is also a component of the translational machinery associated with the 40S ribosomal subunit (Auth and Brawerman, Proc. Natl. Acad. Sci. 89(10) (1992), 4368-72), intracellular staining was performed in parallel after permeabilization of the cells with saponin.

For cell staining and flow cytometry experiments, the human T cell leukemia cell line Jurkat (kindly provided by Dr. G. Moldenhauer, DKFZ Heidelberg, Germany) and the murine neuroblastoma line N2a (kindly provided by Dr. S. Weiss, University Munich, Germany) were used. The Jurkat cells were cultured in RPMI 1640 medium supplemented with 10% heat-inactivated fetal calf serum (FCS), 2 mM L-glutamine, 100 U/mL penicillin G sodium and 100 µg/mL streptomycin sulfate at 37° C. in a humidified atmosphere with 5% $CO_2$. The cell line N2a was cultured in DMEM medium supplemented with 10% heat-inactivated FCS, 0.1 mM non-essential amino acids, 2 mM L-glutamine, 100 U/mL penicillin G sodium and 100 µg/mL streptomycin sulfate (all from Invitrogen, Groningen, The Netherlands) under the same conditions, as indicated for Jurkat cells. For cell surface staining, $1 \times 10^6$ cells were incubated with 0.1 mL phosphate buffered saline (PBS, Invitrogen, Groningen, The Netherlands) supplemented with 2% heat-inactivated FCS and 0.1% sodium azide (Roth, Karlsruhe, Germany) (referred to as a FACS buffer) containing diluted scFv antibodies or polyclonal rabbit serum W3 for 45 min on ice. After washing with FACS buffer, the cells were incubated with 0.1 mL of 0.01 mg/mL anti-$(His)_6$ mouse mAb 13/45/31-2 (Dianova, Hamburg, Germany) in the same buffer for 45 min on ice. After a second washing cycle, the cells were incubated with 0.1 mL of 0.015 mg/mL FITC-conjugated goat anti-mouse IgG antibodies (Dianova, Hamburg, Germany) under the same conditions as before. For the detection of bound W3 rabbit polyclonal antibodies, the cells were incubated with 0.1 mL of 0.015 mg/mL FITC-conjugated goat anti-rabbit IgG antibodies (Dianova, Hamburg, Germany). The cells were then washed again and resuspended in 0.5 mL of FACS buffer containing 2 µg/mL propidium iodide (Sigma-Aldrich, Taufkirchen, Germany) to exclude dead cells.

For intracellular staining, the cells were first fixed with 3% paraformaldehyde (Merck, Darmstadt, Germany), washed with PBS, quenched with PBS containing 50 mM ammonium chloride (Roth, Karlsruhe, Germany) and 20 mM glycine (Sigma-Aldrich, Taufkirchen, Germany) and washed again with PBS. The intracellular staining was performed as described for the cell surface staining except that the FACS buffer was supplemented with 0.1% saponin (Calbiochem, Darmstadt, Germany), all incubation steps were performed at room temperature, and cells were measured in the absence of propidium iodide.

The fluorescence of $1 \times 10^4$ stained cells was measured using a Beckman-Coulter Epics XL flow cytometer (Beckman-Coulter, Krefeld, Germany). Mean fluorescence (F) was calculated using System-II and Expo32 software (Beckman-Coulter, Krefeld, Germany). The results are shown in FIG. 4.

Both scFvs show significant binding to the cell surface of Jurkat and N2a cells. The measured fluorescence signals were comparable with that obtained for W3 serum used as a positive control (in case of N2a cell) or were even stronger (Jurkat cells). Permeabilization of the cells by saponin led to a strong increase in the mean fluorescence intensity, thus indicating the recognition of intracellular LRP. This is most likely due to the large abundance of the 37 kDa LRP in cells (six to eight copies per ribosome) (Auth and Brawerman, 1992).

EXAMPLE 5

Figure 5A:
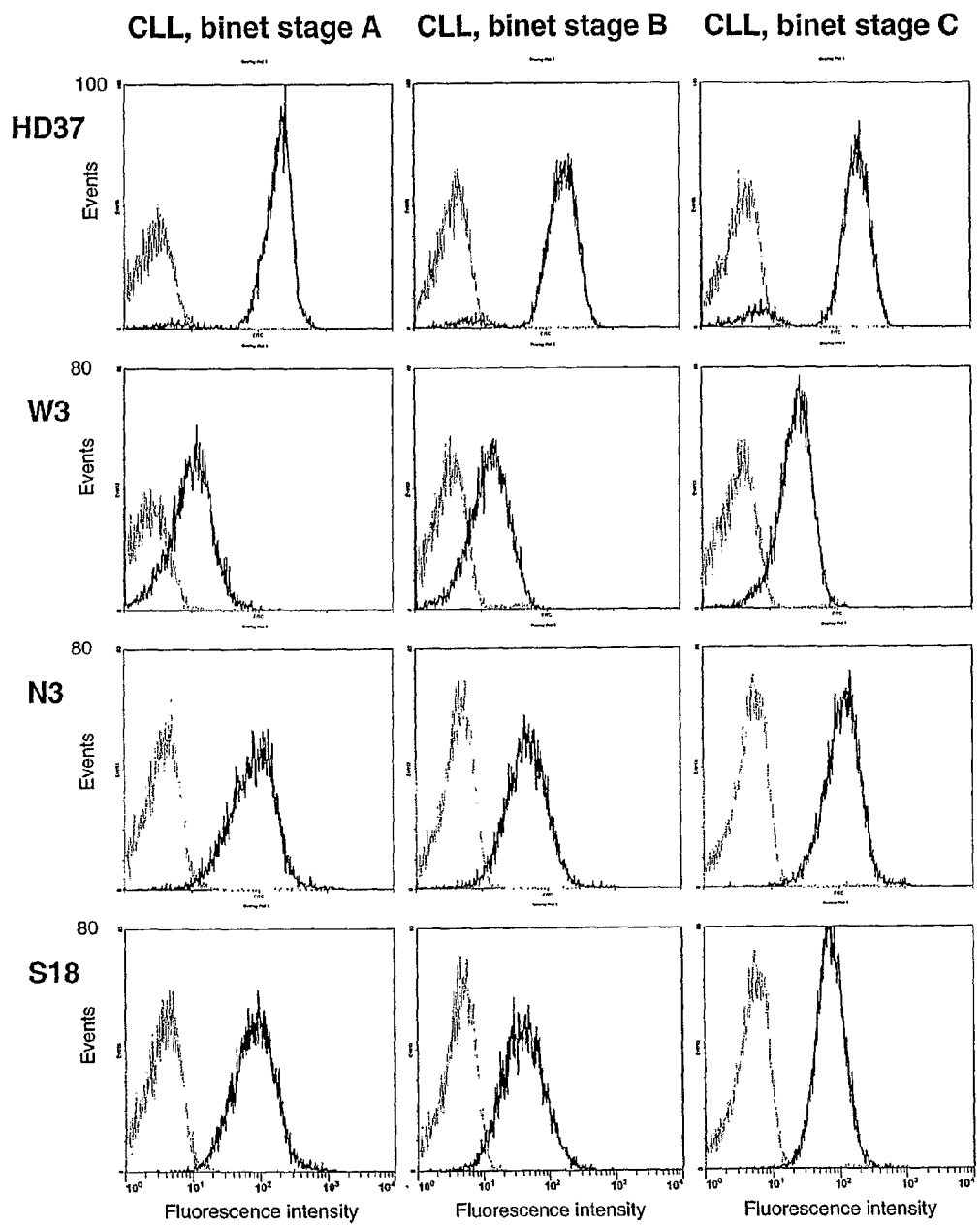
Figure 5B:
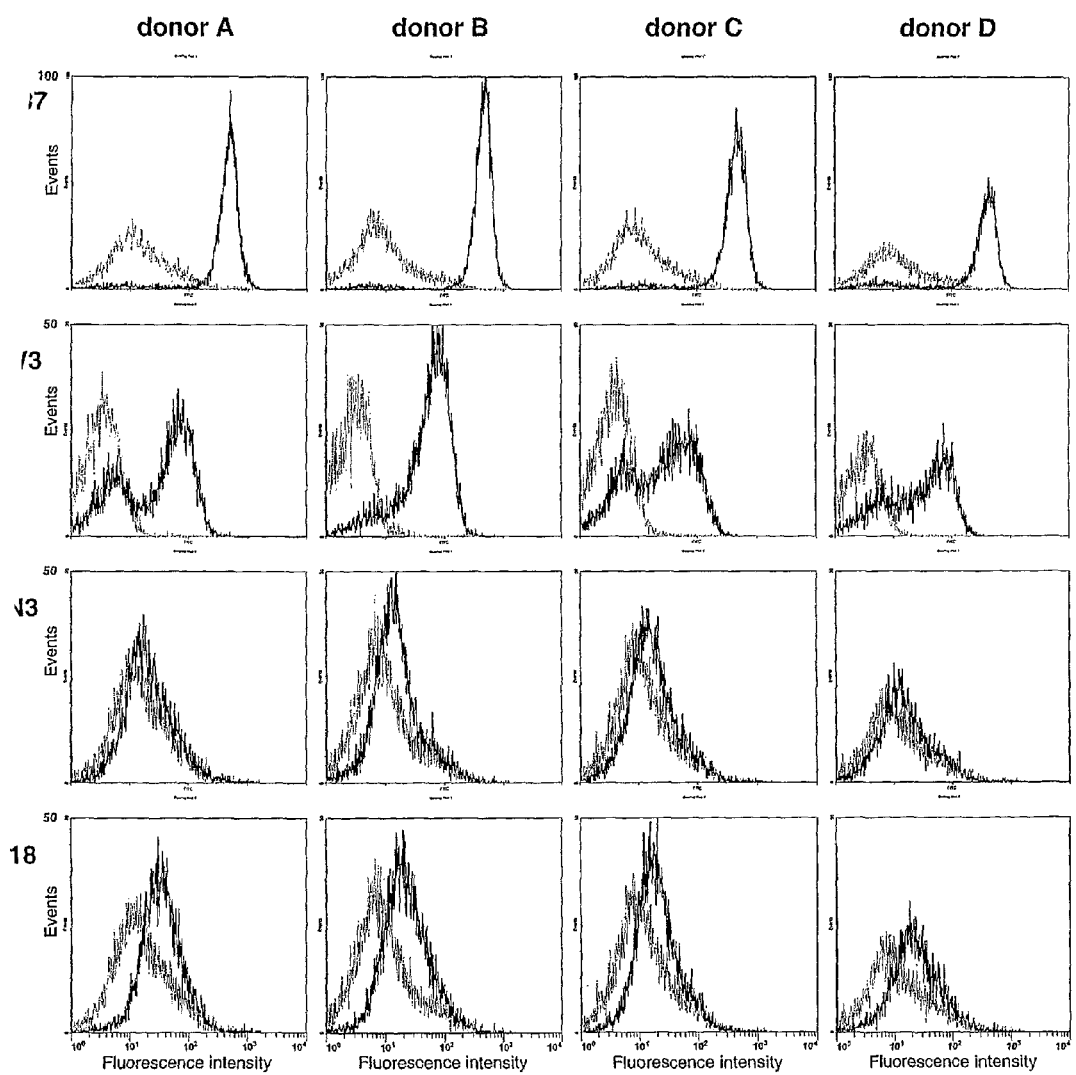

Analysis of Binding of scFv S18 and N3 to the Peripheral Blood Lymphocytes (PBL) from Patients with B-Cell Chronic Lymphocytic Leukemia (B-CLL) and Healthy Donors by Flow Cytometry It was previously demonstrated that LRP is expressed on various hematologic tumor cell lines. In addition, PBMCs isolated from blood samples from patients with B-CLL exhibited significant LRP expression in contrast to samples of healthy donors where no LRP was detectable on $CD19^+$ B cells and $CD5^+$ T cells (Siegel et al., Blood 102(13) (2003) 4416-23). In order to assess whether the scFv antibodies S18 and N3 have the ability to bind LR/LRP on the surface of malignant B-cells, PBMCs from three different CLL patients (Binet stage A-C) were analyzed by flow cytometry (FIG. 5a). As a control, enriched B-cells from 4 healthy donors were used. Peripheral blood mononuclear cells (PBMC) were isolated from heparinized peripheral blood from healthy donors or patients with B-CLL by density gradient centrifugation. Blood samples were twice diluted with PBS (Invitrogen), layered on a cushion of Histopaque-1077 (Sigma-Aldrich) and centrifuged at 800×g for min. PBMCs located in the interface were collected and washed 3 times with PBS before use. The PBMCs were either directly used for antibody staining and flow cytometric analysis or cryoconserved in RPMI 1640 medium supplemented with 40% heat-inactivated FCS (Invitrogen) and 10% DMSO (Sigma-Aldrich) until use. For isolation of B cells from PBMCs from healthy donors, the EasySEP™ negative B cell enrichment kit (CellSystems, St. Katharinen, Germany) was used according to the instructions of the manufacturer.

For cell surface staining, the corresponding cells were first incubated with FACS buffer containing 1 mg/mL human IgG (Sigma-Aldrich) to block the Fc receptors. All following antibody incubations were performed in FACS buffer supplemented with 1 mg/mL human IgG. $1 \times 10^6$ of the cells were incubated with 0.1 mL of either diluted scFv or diluted mAb or the rabbit polyclonal serum W3 for 45 min on ice. After washing with FACS buffer, the cells were incubated with 0.1 mL of 0.01 mg/mL anti-$(His)_6$ mouse mAb 13/45/31-2 (Dianova) in the same buffer for 45 min on ice. After a second washing cycle, the cells were incubated with 0.1 mL of 0.015 mg/mL FITC-conjugated goat anti-mouse IgG antibodies (Dianova, Hamburg, Germany) under the same conditions as before. For detection of bound mouse mAb and W3 rabbit polyclonal antibodies, the cells were incubated with 0.1 mL of 0.015 mg/mL FITC-conjugated goat anti-mouse IgG antibodies (Dianova, Hamburg, Germany) and 0.015 mg/mL FITC-conjugated goat anti-rabbit IgG antibodies (Dianova, Hamburg, Germany), respectively. The cells were then washed again and resuspended in 0.5 mL FACS buffer containing 2 µg/mL propidium iodide (Sigma-Aldrich) to exclude dead cells. The fluorescence of $1 \times 10^4$ stained cells was measured using a Beckman-Coulter Epics XL flow cytometer (Beckman-Coulter). Mean fluorescence (F) was calculated using System-II and Expo32 software (Beckman-Coulter). The results are presented in FIG. 5b.

Staining of PBMCs from B-CLL patients with the scFvs S18 and N3 demonstrated recognition of a large cell population of B-cells, as shown by staining with anti-CD19 antibodies (FIG. 5a). The intensity of staining of the analyzed blood samples did not correlate with the Binet stage of the disease. In contrast, the scFvs S18 and N3 revealed no binding to enriched B-cell populations from four healthy donors (FIG. 5b), although S18 showed slight background binding to B-cells of healthy individuals.

EXAMPLE 6

Affinity Maturation of the Clone S18 by Light Chain Shuffling

To generate anti-LRP scFvs with increased affinity, chain shuffled libraries based on the clone S18 were generated by rearrangement of their respective $V_H$ chains with a $V_L$ gene repertoire.

The $V_\kappa$ and $V_\lambda$ repertoires were excised from pEXHAM1 DNA originating from a large human naïve scFv library previously described (Schwarz et al., 2004). This repertoire reflects approximately $10^5$ individual $V_\kappa$ and $V_\lambda$ chains each. Rearrangement with the parental S18 heavy chain in pEXHAM1 and transformation into E. coli XL1 blue (1.8 kV, 0.1 cm gap cuvette 25FD, 200 Ohm) resulted a $2.23 \times 10^6$ ($V_\kappa$) as well as $5.7 \times 10^7$ ($V_\lambda$) member library for S18.

Since S18 was isolated from the synthetic library it opened the possibility to additionally rearrange the heavy chain with a synthetic light chain repertoire. In this repertoire the E4 light chain is permutated only in the CDR3 permitting all amino acids in 4 to 7 positions (CNSR(N)$_{4-7}$ VLFG). By recombination with the S18 $V_H$ an additional library of $8.27 \times 10^7$ was created.

Sequence analysis of 90 randomly picked clones in total of all three libraries after transformation, showed that each clone contained an individual light chain and 61 clones (66%) revealed expression of full length scFvs detectable by an anti-His antibody (Qiagen, Hilden, Germany) in Western Blot. Four rounds of selection were performed on biotinylated GST-LRP fusion protein, kindly provided by Prof. Weiss (Munich). Prior to selection, each library was consecutively pre-adsorbed to polystyrene coated GST and Streptavidin-coated beads (Dynal, Oslo, Norway), in order to remove potential binders to these proteins. Selection pressure favouring high affinity binders was created by successively limiting the antigen concentration (1st rd 10 nM, 2nd rd 1 nM, 3rd rd 0.1 nM, 4th rd 0.01 nM). All rearranged libraries were kept separately.

Approximately $10^9$ phage from each library, resuspended in PBS, 0.1% tween, 2% skim milk, were incubated with soluble, biotinylated GST-LRP-fusion. Phage antigen complexes were captured by streptavidin-coated magnetic beads (Dynal, Oslo, Norway), using a magnetic separator (Dynal, Oslo, Norway). Unspecific binding phage were removed by ten washing steps with PBS, 0.1% tween. Phage antigen complexes attached to the magnetic beads were used for infection of freshly grown E. coli XL1 Blue cells (mid log. Phase OD$_{600}$ 0.2-0.5). Cells successfully transduced with phagemids encoding the human scFvs were selected for ampicillin resistance and were subsequently infected with M13K07 helper phage to generate phage progeny displaying scFv for the following in vitro selection. After the $4^{th}$ round of selection, individual colonies were grown in LB medium containing 100 µg/mL ampicillin and 20 µg/mL tetracycline at 30° C. in a PP-Masterblock 2 mL (Greiner, Frickenhausen, Germany). Cells were harvested by centrifugation and resuspended in 200 µL 200 mM Tris-HCl, pH 7.5, 20% Sucrose, 1 mM EDTA. During incubation for one hour on ice the outer membrane was destroyed and the soluble periplasmic proteins including the scFv were released into the liquid. After elimination of spheroplasts and cellular debris by centrifugation, the crude periplasmic extracts were tested in ELISA for scFv binding to the LRP-fusion protein.

Detection of scFv bound to GST-LRP-fusion protein (200 ng/well) was carried out by using an anti-Penta His-HRP conjugate (Qiagen, Hilden, Germany; 0.1 µg/mL). The signal was developed with Tetramethyl benzidine solution (TMB) (KPL, Maryland, USA) and detected at 450 nm after stopping the reaction with 0.5 M $H_2SO_4$.

44 clones from each approach were tested in ELISA.

Analysis of the library rearranged with the κ repertoire revealed uniform signal strength of all clones tested, suggesting that one clone was extensively enriched. Sequence analysis showed, that the parental clone was enriched 100% indicating that no superior combination was generated.

Testing individual clones from the approaches containing combinations with the λ- and the synthetic repertoire also revealed very uniform signals with no significant improvement compared to the respective parental clone which was grown and induced in parallel as a reference. Assuming that the scFv were present in saturating amounts, the ELISA was repeated with diluted crude periplasmic extracts but failed to identify differences among the clones. A further approach with higher diluted periplasmic extracts was not feasible due to limitations in the accessibility of the antigen.

8-12 individual clones of each approach were randomly selected for sequencing.

Sequence analysis of the approaches rearranged with the λ repertoire revealed in case of the S18 heavy chain no clear enrichment of a single clone. Only one clone was found twice.

Analysis of clones isolated from the library with the rearranged synthetic repertoire identified 6 identical clones (5-4-31) and two further clones revealing homology in the CDR3 (5-4-1 and 5-4-19). Besides these eight identical or homologues clones, four unique clones were sequenced, showing no apparent sequence homology. FIG. 7 shows an alignment of the CDR3 regions of all individual clones containing synthetic light chains.

EXAMPLE 7

FACS Analysis of Affinity-Matured scFv on Different Cells

Crude periplasmic extracts, prepared from all clones analysed by sequencing, were tested by flow cytometry for their ability to bind LRP on the surface of HEK 293 cells in comparison to their parental scFv clone S18 and N3, respectively (FIG. 8). Since crude periplasmic extracts were used in this assay, differences in signal strength could only be used for a preliminary ranking due to different scFv concentrations in the respective preparation. Several scFv preparations showed significantly higher fluorescence signals, when compared to their respective parental clones that were cultivated in parallel under the same conditions. As expected, the enriched clone (5-4-31) and related homologues (5-4-1 and 5-3-43), derived from the rearrangement with the synthetic repertoire, also reveal improved binding. Clones selected for further characterizations are marked by asterisks.

The scFv were subcloned into the expression vector pSKK2, transformed into *E. coli* RV308, expressed in 2 Liter shake flask cultures and purified by immobilized metal ion affinity chromatography (IMAC) (see example 3). Protein concentration was determined by Bradford and $OD_{2801260}$.

To prove that the improved binding properties of the selected scFv clones are due to improved affinity, and not to higher scFv concentrations in crude preparations, the purified scFv were tested in flow cytometry in equal concentrations on different cell lines (FIG. 9).

The clones 4-4-23, 5-3-43 and 5-4-1 show significant higher signals compared to their parental clones on all cell lines tested. Similar to the anti-LRP monoclonal antibody 43515 (a kind gift of Dr Coggin, University of Alabama) the strongest signals were observed on the human epithelial epidermoid carcinoma cell line A-431 and the human colon carcinoma cell line HT-29. Moderate binding was observed on the murine Lewis lung carcinoma cells (LL/2), while only weak or background staining was found on Chinese hamster ovary cells growing in suspension (CHO-S).

EXAMPLE 8

FACS Analysis of Chain-Shuffled scFv on CLL Cells

The parental anti-LRP scFv N3 and S18 show binding to PBMC from patients with B cell chronic lymphocytic leukaemia (B-CLL) indicating the surface expression of LRP on these leukaemia cells. To determine whether the chain-shuffled scFv exhibit improved binding to CLL cells staining and flow cytometric analysis as described in example 5 was performed.

The results in FIG. 10 clearly demonstrate higher fluorescence signals with chain-shuffled scFv on CLL cells in comparison to the parental scFv N3 and S18 indicating improved binding characteristics of the chain-shuffled scFvs. An improvement of the cell binding is in particular obvious for the clones 5-3-43, 5-4-1 and 5-4-31.

EXAMPLE 9

Characterization of Affinity Matured scFv by Immunocytology

To test whether the anti-LRP scFv are capable of binding to cells fixed on slides, Cytospin experiments were performed using the Biogenix-AP Kit according to the manufacturer's guidelines.

Since flow cytometric analysis revealed strong binding to the colon line HT-29 with the scFv 5-3-43, 5-4-1 and 5-4-31, but only slight or background staining of CHO-S, these two cell lines were selected for these experiments. An anti-CD16 scFv served as a negative control, while a moAb directed against cytokeratin, which stains all cell lines of epithelial origin was used as a positive control.

The negative controls without scFv and the scFv anti-CD16 reveal no staining of the cells, while the anti-cytokeratin moAb showed a clear staining of the cell surface of the colon line HT-29 (FIG. 11). All anti-LRP scFv also reveal unambiguous staining of the cell surface of HT-29, while only slight background staining was observed on CHO-S.

EXAMPLE 10

Expression and Purification of Recombinant GST-LRP Fusion Protein in *E. coli*

In order to obtain sufficient amounts of recombinant LRP, two different constructs were cloned into the expression vector pGEX with an N-terminal GST-fusion. The construct $LRP_{long}$ codes for all amino acids of the extracellular region, while the construct $LRP_{short}$ was cloned according to Narumi et al. 1999, coding for a truncated form.

The respective DNA fragments were amplified by PCR using LRP cDNA (kindly provided by Dr. S. Menard, Milano) as a template and cloned into the EcoRI and BamHI sites of pGEX. After confirmation of sequence integrity the plasmids were transformed into the bacterial strain BL21 for expression. Expression levels were tested for both constructs at 20° C. and 30° C. at different time points after induction. For both fusion proteins the maximal amount of soluble protein was visible after induction at 30° C. for 4-5 hours. Prolonged induction times lead to a loss of the proteins probably due to proteolytic degradation.

800 ml bacterial cultures were induced for $LRP_{short}$, $LRP_{long}$ and GST alone using the determined conditions. After 4.5 h induction the cell pellets were sonicated and the soluble fractions were incubated with Glutathione Sepharose 4 Fast Flow. The GST and GST fusions molecules were eluted with 5 mM reduced Glutathione, 50 mM Tris-HCl pH=8.

Analysis in a Coomassie stained PAA gel under reducing conditions showed 100% purity of the GST molecule with a molecular weight around 25 kDa (calculated 26 kDa). In case of the GST-short (39.3 kDa) and GST-long (48.3 kDa), several bands smaller than the fusion protein were stained. The lowest band revealed a molecular weight comparable to the GST molecule.

Size exclusion analysis on a Superdex 200 column indicated clearly that GST-long formed mainly soluble aggregates of high molecular weight. In contrast, in case of the GST-short molecule the major peak (74.5% of the protein) corresponds to a molecule with a molecular weight around 40 kDa. A second peak (25.5%) with an elution volume of 12.96 ml might reflect a homodimer with a molecular weight around 100 kDa.

Analysis of the molecules by Western Blot using an anti-GST monoclonal antibody stained additional bands representing degradation products of the fusion molecules

EXAMPLE 11

Titration of the scFv S18, 5-3-43, 5-4-1 and 5-4-31 in ELISA on Recombinant LRP

To further demonstrate the improved affinities of the chain shuffled scFv the new molecules were titrated on recombinant GST-LRP fusion protein. FIG. 12 shows the results of the titration. All three chain-shuffled scFv clearly revealed improved binding compared to the parental clone S18.

In order to estimate the affinity, the equation for one-site-binding (hyperbola) $Y=B_{MAX}*X/(K_d+X)$ was used. The $K_D$ was calculated using the GraphPadPrism software. Calculations revealed an improvement of approximately factor 10 for the best clone 5-4-1.

EXAMPLE 12

Conversion of the scFv S18 5-4-1 into a Full Length IgG1 Molecule and Expression and Purification Based on the preceding results, the scFv S18 5-4-1 clone was selected for conversion into a full length IgG1 molecule. For this purpose the variable domains of the light chain and heavy chain were amplified individually and cloned separately into two different mammalian expression vectors, coding for the human constant domains. The vectors used for the cloning were provided by Cambridge Antibody Technology, previously described by Persic et al., 1997.

Analysis of the nucleotide and amino acid sequences of the variable domains S18 5-4-1 scFv was performed, by comparing the sequence to the closest related human germline sequence. Abnormal amino acids were identified probably introduced by PCR primers, cross-reacting with the variable domains of two different families.

PCR primers were designed for amplification of the respective chains, thereby substituting abnormal amino acids residues and introducing appropriate restrictions sites for cloning of the fragments. The PCR products $VH^{S18}$ and $VL^{S18\ 5-4-1}$ sequences were cloned into the mammalian expression vector pEU1.2 and pEU4.2 (λ CL) respectively. Plasmid DNA was prepared from the pEU 1.2 $VH^{S18}$ and pEU $VL^{S18\ 5-4-1}$ using the Qiagen plasmid DNA maxi preparation kit. Identity of the DNA fragments was confirmed by DNA sequencing.

The human anti-LRP IgG1 antibodies with the variable domains from the scFv S18 5-4-1 were produced in human embryonic kidney cell line 293 (HEK-293).

HEK-293 cells (ATCC access number CRL-1573) were cultured in DMEM medium supplemented with 10% heat-inactivated fetal calf serum (FCS), 2 mM L-glutamine, 100 U/mL penicillin G sodium and 100 μg/mL streptomycin sulfate (all from Invitrogen, Karlsruhe, Germany) (referred to as complete DMEM medium) at 37° C. in a humidified atmosphere with 5% $CO_2$. The day before calcium phosphate transfection of the cells, $1.5 \times 10^6$ 293 cells were seeded in a 10 cm diameter cell culture plate (Greiner, Nürtingen, Germany) in 10 mL complete DMEM medium. For transfection of one dish of 293 cells 3 μg of the plasmid encoding the IgG1 heavy chain (pEU 1.2 VH) and 2 μg of the plasmid encoding the IgG1 light chain (pEU 4.2 VL) were mixed with 500 μL 250 mM $CaCl_2$ (Roth, Karlsruhe, Germany). This DNA/$CaCl_2$ mixture was then added dropwise to 500 μL 2×HEBS buffer (280 mM NaCl (Fisher Scientific, Nidderau, Germany), 1.5 mM $Na_2HPO_4$ (Roth), 50 mM HEPES (Roth), adjusted to pH 7.05 with NaOH) and incubated for 15 min at room temperature. After removal of the old DMEM medium from 293 cells, 9 mL complete DMEM medium was added to the transfection cocktail, mixed and transferred to the cells. The next day, the transfection medium was exchanged for serum-free DMEM medium (DMEM medium supplemented with 2 mM L-glutamine, 100 U/mL penicillin G sodium and 100 μg/mL streptomycin sulfate and 1× Insulin-Transferrin-Selenium-A supplement (all from Invitrogen). Supernatants containing the secreted IgG molecules were collected twice in a period of two to six days after transfection, depending on the viability of the cells. After each harvest, fresh serum-free medium was added to the cells. Harvested supernatants were centrifuged to remove cells or cell debris and stored at −80° C. until used for purification of the fusion protein. Transfections were repeated until approximately 2.3 L of supernatant containing IgG1 S18 were harvested.

Purification of the IgG1 molecule was performed on a 1 mL Protein A column (rProtein A Sepharose™ Fast Flow, Amersham Pharmacia). The column was equilibrated with ten volumes DMEM pH 7 (Invitrogen; supplemented with 100 μg/mL Streptomycin, 100 u/ml Penicillin, 1× Insulin-Transferrin-Selenium-A and 2 mM L-Glutamine). Before loading the cell culture supernatant on the column, it was passed through a 0.2 μm sterile filter (Steritop, Millipore) and adjusted to pH 7 by adding 0.1 M glycine/HCl pH 2.7. The column was run by gravity flow at 4° C. Subsequently, the column was washed with 10 volumes DMEM pH 7. Elution was carried out with 6 volumes 0.1 M glycine/HCl pH 2.7. A fraction size of 1 ml was collected directly into 55 μL 1 M Tris/HCl pH 8.8.

The column fractions were analysed in a 12% PAA-gel and IgG containing fractions were pooled and dialysed twice against 5 Liters of PBS pH 7. Bradford protein determination revealed a total yield of 14 mg.

EXAMPLE 13

FACS Analysis of IgG1 S18 5-4-1 on Different Tumor Cell Lines

To test whether the variable binding domains of S18 5-4-1 retained their high affinity binding to cells after conversion into a full-length human IgG1 molecule a titration experiment with the human epidermoid carcinoma cell line A-431 and the colon carcinoma cell line HT-29 was performed. The staining was performed essentially as described in example 4 except that the cell bound human IgG1 antibodies were detected by 15 μg/mL FITC-conjugated goat anti-human IgG. The results of the flow cytometric measurements of $10^4$ living cells were analysed using the GraphPadPrism software and the regression curves together with the measured mean fluorescence values are presented in FIG. 13.

The results obtained on A-431 cells (FIG. 13 A) as well as the results from the colon cell line HT-29 (FIG. 13 B) clearly demonstrate improved binding characteristics for the S18 5-4-1-derived IgG1 antibody in comparison to the scFv S18 5-4-1. The improved binding is most likely the result of the higher affinity of the variable domains in combination with an avidity effect due to bivalent binding of the IgG1 molecule.

The invention claimed is:

1. A method for treating B-cell chronic lymphocytic leukemia, non-Hodgkin's lymphoma, Hodgkin's lymphoma, lung cancer, colon carcinoma, mammary carcinoma, pancreatic carcinoma, prostate cancer, or metastasising cancers, comprising administering to a patient in need thereof a pharmaceutical composition comprising a tandem diabody, wherein said tandem diabody is prepared by non-covalent dimerization of single-chain Fv-antibodies each comprising a $V_H$ and a $V_L$ specific to an epitope of 67 kDa laminin receptor or its 37 kDa precursor and separated by a peptide linker or by no linker, said $V_H$ comprises the amino acid sequence of SEQ ID NO: 4 or 6.

2. The method according to claim 1, wherein said tandem diabody additionally comprises at least one further antigen-interaction site and/or at least one further effector domain.

3. The method according to claim 2, wherein said antigen-interaction site is specific for one or more cell surface molecules.

4. The method according to claim 3, wherein said cell surface molecule is expressed on human NK cells, T cells, monocytes, macrophages or granulocytes.

5. The method according to claim 4, wherein said cell surface molecule is antigen CD2, CD3, CD16, CD64, CD89; NKp30, NKp44, NKp46, NKp80 (KLR-F1), NKG2C or NKG2D.

6. The method according to claim 1, wherein said patient is treated by immunotherapy.

7. The method according to claim 1, wherein said method is for treating B-cell chronic lymphocytic leukaemia.

8. A method for treating B-cell chronic lymphocytic leukemia (B-CLL), non-Hodgkin's lymphoma, Hodgkin's lymphoma, lung cancer, colon carcinoma, mammary carcinoma, pancreatic carcinoma, prostate cancer, or metastasising cancers, comprising administering to a patient in need thereof a pharmaceutical composition comprising an antibody or antigen binding fragment thereof specifically recognizing an epitope of 67 kDa laminin receptor or its 37 kDa precursor, wherein said antibody or antigen binding fragment thereof comprises a variable $V_H$ region comprising the amino acid sequence of SEQ ID NO:6 and a variable $V_L$ region comprising the amino acid sequence of SEQ ID NO:7, wherein the CDR3 of the $V_L$ region from residues 88 to 100 of SEQ ID NO:7 is replaced by residues 9 to 19 of the amino acid sequence selected from the group consisting of SEQ ID NOs: 120, 121, and 125.

9. The method according to claim 8, wherein said antibody or antigen binding fragment thereof additionally comprises at least one further antigen-interaction site and/or at least one further effector domain.

10. The method according to claim 9, wherein said antigen-interaction site is specific for one or more cell surface molecules.

11. The method according to claim 10, wherein said cell surface molecule is expressed on human NK cells, T cells, monocytes, macrophages or granulocytes.

12. The method according to claim 11, wherein said cell surface molecule is the antigen CD2, CD3, CD16, CD64, CD89; NKp30, NKp44, NKp46, NKp80 (KLR-F1), NKG2C or NKG2D.

13. The method according to claim 1, wherein said $V_L$ comprises SEQ ID NO; 5 or 7.

* * * * *